United States Patent
Bichon et al.

[11] Patent Number: 6,124,316
[45] Date of Patent: Sep. 26, 2000

[54] COMPOUNDS WHICH ARE SPECIFIC ANTAGONISTS OF THE HUMAN NK3 RECEPTOR AND THEIR USE AS MEDICINAL PRODUCTS AND DIAGNOSTIC TOOLS

[75] Inventors: Daniel Bichon, Montpellier; Patrick Gueule, Teyran; Didier Van Broeck, Murviel les Montpellier; Xavier Emonds-Alt, Combaillaux; Vincenzo Proietto, Saint Georges D'Orques, all of France

[73] Assignee: Sanofi, Paris, France

[21] Appl. No.: 09/306,825

[22] Filed: May 7, 1999

Related U.S. Application Data

[63] Continuation of application No. 08/880,832, Jun. 23, 1997, abandoned, which is a continuation of application No. 08/405,833, Mar. 17, 1995, abandoned.

[30] Foreign Application Priority Data

Mar. 18, 1994 [FR] France ................... 94 03193
Jul. 29, 1994 [FR] France ................... 94 09478
Jan. 19, 1995 [FR] France ................... 95 00571

[51] Int. Cl.$^7$ .............. A61K 31/445; C07D 401/02; C07D 401/14
[52] U.S. Cl. .............. 514/316; 514/212; 514/278; 514/318; 514/326; 514/330; 514/331; 540/524; 540/597; 540/598; 546/17; 546/186; 546/187; 546/188; 546/189; 546/190; 546/191; 546/208
[58] Field of Search .............. 540/524, 597, 540/598; 546/17, 186, 187, 188, 189, 190, 191, 208; 514/212, 278, 316, 318, 326, 330, 331

[56] References Cited

U.S. PATENT DOCUMENTS 5,340,822  8/1994  Emonds-Alt et al. ................. 514/316

FOREIGN PATENT DOCUMENTS 714891  6/1996  European Pat. Off. .

OTHER PUBLICATIONS

Maggi et al. "Tachykinin receptors and tachykinin recptor antagonists" J. Auton. Pharm. v. 13, p.23–93, 1993.

Primary Examiner—Ceila Chang
Attorney, Agent, or Firm—Bacon & Thomas

[57] ABSTRACT

A compound of formula:

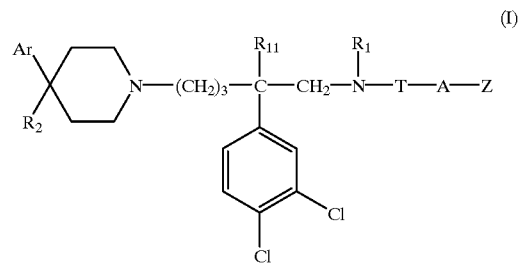

(I)

in which:

Ar represents a pyrid-2-yl or a phenyl which is unsubstituted or substituted by a halogen, a methyl or a ($C_1$–$C_4$) alkoxy;

$R_1$ represents a methyl group;

$R_{11}$ represents hydrogen;

or $R_1$ and $R_{11}$ together represent a —$(CH_2)_3$— group;

$R_2$ represents a hydroxyl; a ($C_1$–$C_7$)alkoxy; a ($C_1$–$C_7$) acyloxy; a cyano; an —$NR_6R_7$ group; an —$NR_3COR_4$ group; an —$NR_3COOR_8$ group; an —$NR_3SO_2R_9$ group; an —$NR_3CONR_{10}R_{12}$ group; a ($C_1$–$C_7$)acyl group; a ($C_1$–$C_7$)alkoxycarbonyl; a —$CONR_{10}R_{12}$ group; a —$CH_2OH$ group; a ($C_1$–$C_7$)alkoxymethyl; a ($C_1$–$C_7$)acyloxymethyl; a ($C_1$–$C_7$) alkylaminocarbonyloxymethyl; a —$CH_2NR_{13}R_{14}$ group; a —$CH_2NR_3COR_4$ group; a —$CH_2NR_3COOR_8$ group; a —$CH_2NR_3SO_2R_9$ group; a —$CH_2NR_3CONR_{10}R_{12}$ group; or $R_2$ constitutes a double bond between the carbon atom to which it is attached and the adjacent carbon atom of the piperidine ring;

or Ar and $R_2$, together with the carbon atom to which they are attached, constitute a group of formula:

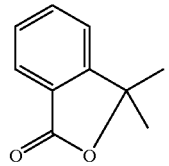

which is $NK_3$ antagonists.

12 Claims, No Drawings

COMPOUNDS WHICH ARE SPECIFIC ANTAGONISTS OF THE HUMAN NK3 RECEPTOR AND THEIR USE AS MEDICINAL PRODUCTS AND DIAGNOSTIC TOOLS

This application is a continuation of U.S. Ser. No. 08/880,832 filed Jun. 23, 1997, now abandoned, which is a continuation of U.S. Ser. No. 08/405,833 filed Mar. 17, 1995, now abandoned.

The subject of the present invention is new compounds which are selective antagonists of the human $NK_3$ receptor and their use for the preparation of medicinal products useful in the treatment of psychiatric diseases, of diseases of psychosomatic origin, of hypertension and, generally, of any central or peripheral pathology in which neurokinin B and the $NK_3$ receptor are involved in interneuronal regulation.

During the past few years, many research studies have been carried out on tachyktnins and their receptors. Tachykinins are distributed both in the central nervous system and in the peripheral nervous system. The tachykinin receptors have been recognized and are classified into three types: $NK_1$, $NK_2$, $NK_3$. Substance P (SP) is the endogenous ligand for the $NK_1$ receptors, neurokinin A ($NK_A$) that for the $NK_2$ receptors and neurokinin B ($NK_B$) that for the $NK_3$ receptors.

The $NK_1$, $NK_2$, $NK_3$ receptors have been identified in various species. Thus, the $NK_3$ receptors have been identified in guinea pigs, rats, monkeys (Br. J. Pharmacol., 1990, 99, 767–773; Neurochem. Int., 1991, 18, 149–165); more recently, they were also identified in man (FEBS Letters, 1992, 299 (1), 90–95).

A recent review by C. A. Maggi et al. presents a summary of the findings on the tachykinin receptors and their antagonists and describes the pharmacological studies and the applications on human therapy (J. Autonomic Pharmacol., 1993, 13, 23–93).

Among the specific antagonists of the $NK_1$ receptor, there may be mentioned the following nonpeptide compounds: CP-96345 (J. Med. Chem., 1992, 35, 2591–2600), RP-68651 (Proc. Natl. Acad. Sci. USA, 1991, 88, 10208–10212), SR 140333 (Curr. J. Pharmacol., 1993, 250, 403–413).

For the $NK_2$ receptor, a selective nonpeptide antagonist, SR 48968 has been described in detail (Life Sci., 1992, 50, PL101–PL106).

As regards the $NK_3$ receptor, some nonpeptide compounds, antagonists for Angiotensin II, have been described, up until now, as having affinity for rat and guinea pig brain $NK_3$ receptor; this affinity is very low and corresponds to an inhibition constant Ki of the order of $10^{-5}M$ (FASEB J., 1993, 7 (4), A 710, 4104). A peptide antagonist [$Trp^7$, $Ala^8$]$NK_A$, weakly specific for rat $NK_3$ receptor has also been described (J. Autonomic Pharmacol., 1993, 13, 23–93).

In Patent Application EP 512901, it is indicated that 5-[2-(4-hydroxy-4-phenylpiperid-1-yl)ethyl]-5-(3,4-dichlorophenyl)-1-benzylpiperid-2-one hydrochloride, called hereinafter compound A, antagonizes the binding of eledoisin with a Ki of 200 nanomolar, eledoisin being a peptide of batrachian origin equivalent to neurokinin B.

Patent Application EP 474561 describes neurokinin antagonists, more particularly $NK_1$ or $NK_2$ receptor antagonists; in particular this application describes N-methyl-N-[2-(3,4-dichlorophenyl)-5-(4-hydroxy-4-phenylpiperid-1-yl)pentyl]benzamide hydrochloride.

None of the peptide or nonpeptide compounds known up until now have a high affinity for the human $NK_3$ receptor.

Pharmacological studies of the peptide and nonpeptide antagonists of the $NK_1$ and $NK_2$ receptors have shown that their affinities for these receptors as well as their pharmacological activities were very highly a function of the species, most probably as a result of small differences in the aminoacid sequences, thereby inducing very fine structural variations in these receptors from one species to another (J. Autonomic Pharmacol., 1993, 13, 23–93). Some experimental data, confirmed by the pharmacological characterization of the compounds which are the subject of the present invention, appear to indicate that a comparable situation exists for the $NK_3$ receptor. In particular, human $NK_3$ receptor is different from rat $NK_3$ receptor.

Nonpeptide compounds have now been found which have a very high affinity for the human $NK_3$ receptor and a high specificity for said receptor. These compounds can be used for the preparation of medicinal products which are useful in the treatment of psychiatric diseases or of diseases of psychosomatic origin and of all central or peripheral diseases in which neurokinin B and the $NK_3$ receptor are involved in interneuronal regulation.

Very high affinity for the human $NK_3$ receptor is understood to mean an affinity characterized by an inhibition constant Ki which is generally less than $5 \cdot 10^{-9}$ M.

In studies on the binding of a ligand, the inhibition constant Ki is defined by the Cheng-Prusoff equation (in Receptor Binding in Drug Research, eds. R. A. O'BRIEN. Marcel Dekker, New York, 1986):

$$Ki = \frac{IC_{50}}{1 + \frac{[L]}{Kd}}$$

[L]: ligand concentration

Kd: dissociation constant of the ligand, $IC_{50}$: concentration which inhibits 50% of the ligand binding.

By high specificity for the human $NK_3$ receptor, it is understood that the inhibition constant (Ki) for the human $NK_3$ receptor is generally at least 100 times lower than the inhibition constant (Ki) for the $NK_2$ receptor or than that for the $NK_1$ receptor of different species.

Disease of psychosomatic origin designates diseases having their origin in the central nervous system (CNS) and pathological consequences at the peripheral level.

Thus, according to one of its aspects, the subject of the present invention is compounds of formula:

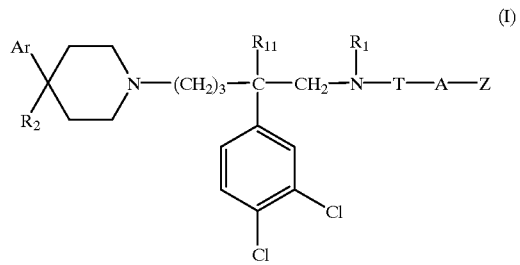

(I)

in which:

Ar represents a pyrid-2-yl or a phenyl which is unsubstituted or substituted by a halogen, a methyl or a ($C_1$–$C_4$) alkoxy;

$R_1$ represents the methyl group;

$R_{11}$ represents hydrogen;

or $R_1$ and $R_{11}$ together represent a —$(CH_2)_3$— group;

$R_2$ represents a hydroxyl; a $(C_1-C_7)$alkoxy; a $(C_1-C_7)$acyloxy; a cyano; an —$NR_6R_7$ group; an —$NR_3COR_4$ group; an —$NR_3COOR_8$ group; an —$NR_3SO_2R_9$ group; an —$NR_3CONR_{10}R_{12}$ group; a $(C_1-C_7)$acyl group; a $(C_1-C_7)$alkoxycarbonyl; a —$CONR_{10}R_{12}$ group; a —$CH_2OH$ group; a $(C_1-C_7)$alkoxymethyl; a $(C_1-C_7)$acyloxymethyl; a $(C_1-C_7)$alkylaminocarbonyloxymethyl; a —$CH_2NR_{13}R_{14}$ group; a —$CH_2NR_3COR_4$ group; a —$CH_2NR_3COOR_8$ group; a —$CH_2NR_3SO_2R_9$ group; a —$CH_2NR_3CONR_{10}R_{12}$ group; or $R_2$ constitutes a double bond between the carbon atom to which it is attached and the adjacent carbon atom of the piperidine ring;

or Ar and $R_2$, together with the carbon atom to which they are attached, constitute a group of formula:

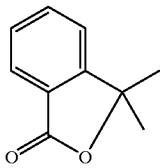

$R_3$ represents a hydrogen or a $(C_1-C_4)$alkyl;

$R_4$ represents a hydrogen, a $(C_1-C_7)$alkyl, a phenyl, a benzyl, a pyridyl or a $(C_3-C_7)$cycloalkyl which is unsubstituted or substituted by one or more methyls;

or $R_3$ and $R_4$ together represent a $(CH_2)_n$ group;

n is 3 or 4;

T represents a methylene, a carbonyl, a —COO— group, a —$CONR_5$— group;

A represents a direct bond, a methylene, an ethylene, a propylene, a vinylene;

or —T—A— represents the —$SO_2$— group

Z represents a phenyl which is unsubstituted or substituted one or several times by a halogen, a $(C_1-C_4)$alkyl, a $(C_1-C_4)$alkoxy, a nitro;

$R_5$ represents a hydrogen or a $(C_1-C_4)$alkyl;

$R_6$ and $R_7$ each represent independently a hydrogen or a $(C_1-C_7)$alkyl; $R_7$ can furthermore represent a $(C_3-C_7)$cycloalkylmethyl, a benzyl or a phenyl; or $R_6$ and $R_7$, together with the nitrogen atom to which they are attached, constitute a heterocycle chosen from azetidine, pyrrolidine, piperidine, morpholine, thiomorpholine or perhydroazepine;

$R_8$ represents a $(C_1-C_7)$alkyl or a phenyl;

$R_9$ represents a $(C_1-C_7)$alkyl; an amino which is free or substituted by one or two $(C_1-C_7)$alkyls; a phenyl which is unsubstituted or substituted once or several times by a substituent chosen from: a halogen atom, a $(C_1-C_7)$alkyl, a trifluoromethyl, a hydroxyl, a $(C_1-C_7)$alkoxy, a carboxyl, a $(C_1-C_7)$alkoxycarbonyl, a $(C_1-C_7)$alkylcarbonyloxy, a cyano, a nitro, an amino which is free or substituted by one or two $(C_1-C_7)$alkyls, the said substituents being identical or different;

$R_{10}$ and $R_{12}$ each represent independently a hydrogen or a $(C_1-C_7)$alkyl; $R_{12}$ may furthermore represent a $(C_3-C_7)$cycloalkyl, a $(C_3-C_7)$cycloalkylmethyl, a hydroxyl, a $(C_1-C_4)$alkoxy, a benzyl or a phenyl; or $R_{10}$ and $R_{12}$, together with the nitrogen atom to which they are attached, constitute a heterocycle chosen from azetidine, pyrrolidine, piperidine, morpholine, thiomorpholine or perhydroazepine;

$R_{13}$ and $R_{14}$ each represent independently a hydrogen or a $(C_1-C_7)$alkyl; $R_{14}$ may furthermore represent a $(C_3-C_7)$cycloalkylmethyl or a benzyl;

provided that:

1/ when Ar is a phenyl group, $R_2$ is a hydroxyl group, T—A—Z is the benzoyl group, $R_1$ is different from the methyl group;

2/ when Ar is the phenyl group, $R_2$ is the —NH—CO—$CH_3$ group, T—A—Z is the benzoyl group, $R_1$ and $R_{11}$ together do not form the —$(CH_2)_3$— group;

3/ when Ar is a phenyl group, $R_2$ is a hydroxyl group, T—A—Z is the 3-methoxybenzyl group, $R_1$ and $R_{11}$ together do not form the —$(CH_2)_3$— group;

as well as their salts.

In the present description, the alkyl groups or the alkoxy groups are straight or branched; halogen is understood to mean a fluorine, chlorine, bromine or iodine atom, preferably a fluorine, chlorine or iodine atom.

In the present description, acyl is understood to mean a formyl or a $(C_1-C_6)$alkylcarbonyl.

The salts of the compounds of formula (I) comprise both those with inorganic or organic acids which allow a suitable separation or crystallization of the compounds of formula (I), such as picric acid or oxalic acid or an optically active acid, for example mandelic or camphosulfonic acid, and those which form pharmaceutically acceptable salts.

The pharmaceutically acceptable salts are such as hydrochloride, hydrobromide, sulfate, hydrogen sulfate, dihydrogen phosphate, methanesulfonate, methyl sulfate, maleate, fumarate, 2-naphthalenesulfonate, benzenesulfonate, glycolate, gluconate, citrate, isethionate, para-toluenesulfonate.

The present invention encompasses the compounds of formula (I) either in racemic form or in pure enantiomeric form.

Depending on the meaning of $R_1$ and $R_{11}$, the compounds of the invention belong to one of the families described below of formulae:

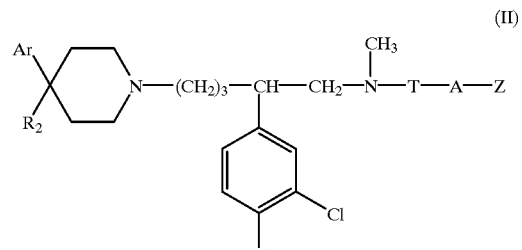

(II)

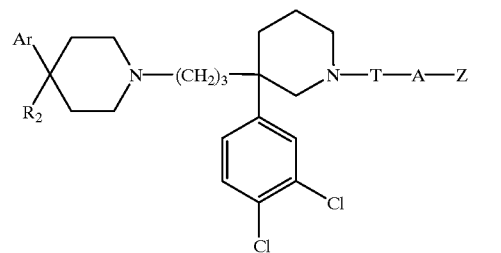

(III)

in which:

Ar, $R_2$, T, A and Z have the meanings given above for (I).

The compounds of formula (I) in which:

Ar represents a pyrid-2-yl or a phenyl which is unsubstituted or substituted by a halogen;

$R_1$ represents a methyl group;

$R_{11}$ represents hydrogen;

or $R_1$ and $R_{11}$ together represent a —$(CH_2)_3$— group;

$R_2$ represents a hydroxyl, a ($C_1$–$C_7$)alkoxy, an amino, a ($C_1$–$C_7$)acyloxy, an —$NR_3COR_4$ group, or $R_2$ constitutes a double bond between the carbon atom to which it is attached and the adjacent carbon atom of the piperidine ring;

$R_3$ represents a hydrogen or a ($C_1$–$C_4$)alkyl;

$R_4$ represents a hydrogen, a ($C_1$–$C_7$)alkyl, a phenyl, a pyridyl or a ($C_3$–$C_7$)cycloalkyl which is unsubstituted or substituted by one or more methyls;

or $R_3$ and $R_4$ together represent a —$(CH_2)_n$— group;

n is 3 or 4;

T represents a methylene, a carbonyl, a —COO— group, a —$CONR_5$— group;

A represents a direct bond, a methylene, an ethylene, a propylene, a vinylene;

or —T—A— represents the —$SO_2$— group

Z represents a phenyl which is unsubstituted or substituted once or several times by a halogen, a ($C_1$–$C_4$) alkyl, a ($C_1$–$C_4$)alkoxy, a nitro;

$R_5$ represents a hydrogen or a ($C_1$–$C_4$)alkyl;

provided that:

1/ when Ar is a phenyl group, $R_2$ is a hydroxyl group, T—A—Z is the benzoyl group, $R_1$ is different from the methyl group;

2/ when Ar is the phenyl group, $R_2$ is the —NH—CO—$CH_3$ group, T—A—Z is the benzoyl group, $R_1$ and $R_{11}$ together do not form the —$(CH_2)_3$— group;

3/ when Ar is a phenyl group, $R_2$ is a hydroxyl group, T—A—Z is the 3-methoxybenzyl group, $R_1$ and $R_{11}$ together do not form the —$(CH_2)_3$— group;

as well as their salts;

are preferred compounds.

The compounds of formula (II) in which $R_2$ is an acetamido, a propionylamino, a butyrylamino, an isobutyrylamino, an acetyl-N-methylamino, a propionyl-N-methylamino, a butyryl-N-methylamino, an isobutyryl-N-methylamino and T—A—Z is a benzyloxycarbonyl which is unsubstituted or substituted on the phenyl by a chlorine or a nitro are also preferred.

The compounds of formula (III) in which Ar represents a phenyl which is unsubstituted or substituted by a halogen, $R_2$ represents a ($C_1$–$C_8$) acylamino, an acyl-N-methylamino in which the acyl is n $C_1$–$C_8$, T—A—Z represents a benzoyl, are also referred compounds.

Thus, the following compounds:

1-benzoyl-3-(3,4-dichlorophenyl)-3-[3-(4-(acetyl-N-methylamino)-4-phenylpiperidin-1-yl)propyl] piperidine, 1-benzoyl-3-(3,4-dichlorophenyl)-3-[3-(4-propionylamino-4-phenylpiperidin-1-yl)propyl] piperidine, 1-benzoyl-3-(3,4-dichlorophenyl)-3-[3-(4-propionyl-N-methylamino)-4-phenylpiperidin-1-yl)propyl] piperidine, 1-benzoyl-3-(3,4-dichlorophenyl)-3-[3-(4-butyrylamino-4-phenylpiperidin-1-yl)propyl]piperidine, 1-benzoyl-3-(3,4-dichlorophenyl)-3-[3-(4-butyryl-N-methylamino)-4-phenylpiperidin-1-yl)-propyl] piperidine, 1-benzoyl-3-(3,4-dichlorophenyl)-3-[3-(4-isobutyrylamino-4-phenylpiperidin-1-yl)propyl]-piperidine, 1-benzoyl-3-(3,4-dichlorophenyl)-3-[3-(4-isobutyryl-N-methylamino)-4-phenylpiperidin-1-yl)propyl] piperidine, 1-benzoyl-3-(3,4-dichlorophenyl)-3-[3-(4-valerylamino-4-phenylpiperidin-1-yl)propyl]piperidine, 1-benzoyl-3-(3,4-dichlorophenyl)-3-[3-(4-valeryl-N-methylamino)-4-phenylpiperidin-1-yl)propyl] piperidine, 1-benzoyl-3-(3,4-dichlorophenyl)-3-[3-(4-isovalerylamino-4-phenylpiperidin-1-yl)propyl] piperidine, 1-benzoyl-3-(3,4-dichlorophenyl)-3-[3-(4-isovaleryl-N-methylamino)-4-phenylpiperidin-1-yl)propyl] piperidine, 1-benzoyl-3-(3,4-dichlorophenyl)-3-[3-(4-pivaloylamino-4-phenylpiperidin-1-yl)propyl] piperidine, 1-benzoyl-3-(3,4-dichlorophenyl)-3-[3-(4-pivaloyl-N-methylamino)-4-phenylpiperidin-1-yl)propyl] piperidine, in the form of racemates or one of their (+) or (−) enantiomers and their salts are particularly preferred.

1-Benzoyl-3-(3,4-dichlorophenyl)-3-[3-(4-(acetyl-N-methylamino)-4-phenylpiperidin-1-yl)propyl]piperidine hydrochloride, in optically pure form, preferably in the form of the (+) isomer, is most particularly preferred.

Among the compounds of formula (II), those in which:

either $R_2$ represents a ($C_5$–$C_7$)alkoxy, a ($C_5$–$C_7$)acyloxy, an —$NR_3COR_4$ group with $R_4$ other than ($C_1$–$C_6$)alkyl when $R_3$ is hydrogen, an —$NR_6R_7$ group with $R_6$ and $R_7$ other than H or ($C_1$–$C_4$)alkyl, an —$NR_3COOR_8$ group, an —$NR_3SO_2R_9$ group, an —$NR_3CONR_{10}R_{12}$ group, a ($C_5$–$C_7$)acyl, a ($C_5$–$C_7$)alkoxycarbonyl, a —$CONR_{10}R_{12}$ group, a ($C_1$–$C_7$)alkoxymethyl, a ($C_1$–$C_7$)acyloxymethyl, a ($C_1$–$C_7$)alkylaminocarbonyloxymethyl, a —$CH_2NR_{13}R_{14}$ group with $R_{13}$ and $R_{14}$ other than hydrogen, a —$CH_2NR_3COR_4$ group with $R_4$ other than ($C_1$–$C_3$) alkyl when $R_3$ is hydrogen, a —$CH_2NR_3COOR_8$ group, a $CH_2NR_3SO_2R_9$ group, a —$CH_2NR_3CONR_{10}R_{12}$ group, or T represents a methylene, or a —$CONR_5$— group with $R_5$ other than hydrogen, or —T—A— represents the —$SO_2$— group form a preferred group of the compounds of the invention.

Among the compounds of formula (III), those in which:

either $R_2$ represents a ($C_5$–$C_7$)alkoxy, a ($C_5$–$C_7$)acyloxy, an —$NR_3COR_4$ group, with $R_4$ other than hydrogen or ($C_1$–$C_3$)alkyl, an —$NR_6R_7$ group with $R_6$ and $R_7$ other than H or ($C_1$–$C_4$)alkyl or, when $R_6$ and $R_7$ together with the nitrogen atom to which they are attached constitute a heterocycle, other than pyrrolidine, piperidine or morpholine, an —$NR_3COOR_9$ group, an —$NR_3SO_2R_9$ group, an —$NR_3CONR_{10}R_{12}$ group, a ($C_1$–$C_7$)acyl, a ($C_5$–$C_7$)alkoxycarbonyl, a —$CONR_{10}R_{12}$ group, a —$CH_2OH$ group, a ($C_1$–$C_7$) alkoxymethyl, a ($C_1$–$C_7$)acyloxymethyl, a ($C_1$–$C_7$) alkylaminocarbonyloxymethyl, a —$CH_2NR_{13}R_{14}$ group, a —$CH_2NR_3COR_4$ group, an —$NR_3COOR_8$ group, a —$CH_2NR_3COOR_8$ group, a —$CH_2NR_3SO_2R_9$ group, a —$CH_2NR_3CONR_{10}R_{12}$ group, or T represents a —$CONR_5$— group, a —COO— group, or A represents a vinylene, or —T—A— represents the —$SO_2$— group form another preferred group of the compounds of the invention.

Particularly preferred are the compounds of formula (IV):

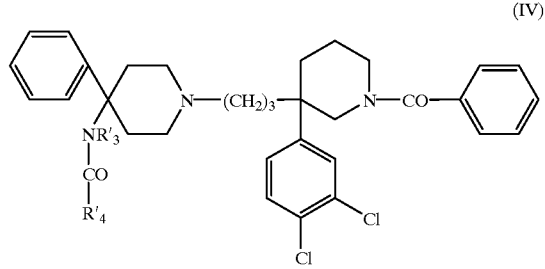

in which:

R'$_3$ represents a hydrogen or methyl;

R'$_4$ represents a (C$_4$–C$_7$)alkyl, a phenyl, a benzyl, a pyridyl or a (C$_3$–C$_7$)cycloalkyl which is unsubstituted or substituted by one or more methyls;

or R'$_3$ and R'$_4$ together represent a —(CH$_2$)$_n$— group;

n is 3 or 4;

as well as their salts.

The salts of compounds of formulae (II), (III) and (IV) according to the present invention comprise both those with organic or inorganic acids which permit suitable separation or crystallization of the compounds of formulae (II), (III) and (IV), such as picric acid or oxalic acid or an optically active acid, for example a mandelic or camphosulfonic acid, and those which form pharmaceutically acceptable salts as described above for the compounds of formula (I).

1-Benzoyl-3-(3,4-dichlorophenyl)-3-[3-(4-pivaloylamino-4-phenylpiperidin-1-yl)propyl] piperidine, 1-benzoyl-3-(3,4-dichlorophenyl)-3-[3-(4-benzoylamino-4-phenylpiperidin-1-yl)propyl]piperidine, 1-benzoyl-3-(3,4-dichlorophenyl)-3-[3-(4-(acetyl-N-methylamino)-4-phenylpiperidin-1-yl)propyl] piperidine, 1-benzoyl-3-(3,4-dichlorophenyl)-3-[3-(4-(pyrid-2-yl) carboxamido-4-phenylpiperidin-1-yl)propyl] piperidine, 1-benzoyl-3-(3,4-dichlorophenyl)-3-[3-(4-(isobutyryl-N-methylamino)-4-phenylpiperidin-1-yl)propyl] piperidine, 1-benzoyl-3-(3,4-dichlorophenyl)-3-[3-(4-valerylamino-4-phenylpiperidin-1-yl)propyl]piperidine, 1-benzoyl-3-(3,4-dichlorophenyl)-3-[3-(4-(propionyl-N-methylamino)-4-phenylpiperidin-1-yl)propyl] piperidine, 1-benzoyl-3-(3,4-dichlorophenyl)-3-[3-(4-(butyryl-N-methylamino)-4-phenylpiperidin-1-yl)propyl] piperidine, 1-benzoyl-3-(3,4-dichlorophenyl)-3-[3-(4-(valeryl-N-methylamino)-4-phenylpiperidin-1-yl)propyl] piperidine, 1-benzoyl-3-(3,4-dichlorophenyl)-3-[3-(4-(isovaleryl-N-methylamino)-4-phenylpiperidin-1-yl)propyl] piperidine, 1-benzoyl-3-(3,4-dichlorophenyl)-3-[3-(4-pivaloyl-N-methylamino)-4-phenylpiperidin-1-yl)propyl] piperidine, in the form of racemates or of one of their (+) or (−) enantiomers, and their salts are particularly preferred compounds according to the present invention.

The compounds according to the invention are obtained by known methods, in particular those which are described in Patent Applications EP 474 561 and EP 512 901.

One of the processes which is suitable for producing the compounds of formula (I) is described below. According to this process a) a compound of formula:

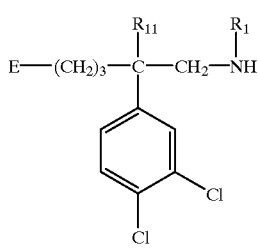

in which $R_1$, $R_{11}$ have the definitions given above for the compounds of formula (I) and E represents a hydroxyl or optionally an O-protected group such as for example a tetrahydropyran-2-yloxy, a benzoyloxy or a (C$_1$–C$_4$)alkylcarbonyloxy or a group:

in which Ar is as defined above and R'$_2$ represents R$_2$ as defined above for (I) or a precursor of R$_2$, it being understood that when R'$_2$ is a hydroxyl or an amino group, these groups may be protected, is treated either with a functional derivative of an acid of formula:

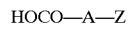

in which A and Z are as defined above for (I), when it is necessary to prepare a compound of formula (I) where T— is —CO—, or with a halogenated derivative of formula:

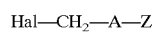

in which Hal represents a halogen, preferably bromine or chlorine, when it is necessary to prepare a compound of formula (I) where T is —CH$_2$—:

or with a chloroformate of formula:

when it is necessary to prepare a compound of formula (I) where T is —COO—, or with an isocyanate derivative of formula:

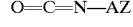

when it is necessary to prepare a compound of formula (I) where T is —CONH—, or with a carbamoyl chloride of formula:

$$ClCON(R_5)-A-Z \quad \quad 7$$

when it is necessary to prepare a compound of formula (I) where T is —CONR$_5$— with R$_5$ different from hydrogen,
or with a benzenesulfonyl chloride of formula $$ClSO_2-Z \quad \quad 7a$$

when it is necessary to prepare a compound of formula (I) in which —T—A— is —SO$_2$— in order to obtain a compound of formula:

$$E-(CH_2)_3-C(R_{11})(Ar')-CH_2-N(R_1)-T-A-Z \quad \quad 8$$

(where Ar' = 3,4-dichlorophenyl)

b) the O-protecting group is optionally removed by the action of an acid or of a base,
c) the alcohol thus obtained of formula:

$$HO-(CH_2)_3-C(R_{11})(Ar')-CH_2-N(R_1)-T-A-Z \quad \quad 9$$

is treated with a compound of the formula:

$$W-SO_2-Cl \quad \quad 9a$$

in which W represents a methyl, phenyl, tolyl or trifluoromethyl group,
d) the sulphonate thus obtained of formula:

$$W-SO_2-O-(CH_2)_3-C(R_{11})(Ar')-CH_2-N(R_1)-T-A-Z \quad \quad 10$$

is reacted with a secondary amine of formula:

$$\text{Ar, R'}_2\text{-piperidine-NH} \quad \quad 11$$

in which Ar and R'$_2$ are as defined above,
e) after optional deprotection of the hydroxyl or of the amino represented by R'$_2$ or possible conversion of R'$_2$ to R$_2$, the product obtained is optionally converted to one of its salts.

In step c) the compound 2a is advantageously methanesulfonyl chloride and therefore, in the compound 10 of step d), W is advantageously a methyl group.

When, in the compound of formula 1, E represents a group:

$$\text{Ar, R'}_2\text{-piperidine-N—}$$

the process comprises only steps a) and e).

According to a variant of the process,
a1) the amine function of the compound of formula 1 is protected by a protecting group in order to prepare a compound of formula:

$$E-(CH_2)_3-C(R_{11})(Ar')-CH_2-NPr(R_1) \quad \quad 12$$

in which E, R$_1$, R$_{11}$ are as defined above and Pr represents a nitrogen-protecting group, for example a tert-butoxycarbonyl (Boc), a trityl, a benzyl, b1) the O-protecting group is optionally removed by the action of an acid or of a base,
c1) the alcohol thus obtained of formula:

$$HO-(CH_2)_3-C(R_{11})(Ar')-CH_2-NPr(R_1) \quad \quad 13$$

is treated with a compound of formula 9a described above, d1) the sulfonate of formula:

14

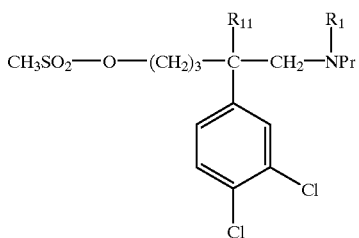

thus obtained is reacted with a secondary amine:

11

to give the compound of formula:

15

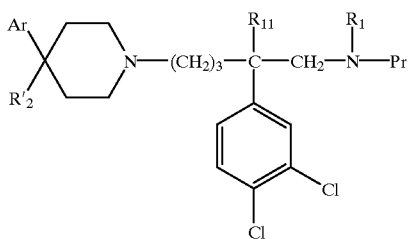

e1) the nitrogen is deprotected in acidic medium,
f1) the compound of formula:

16

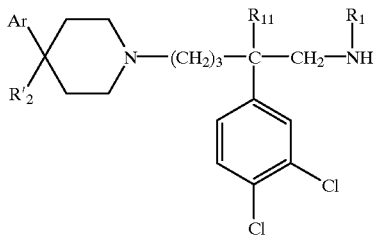

thus obtained is treated with one of the compounds 3, 4, 5, 6, 7 or 7a described above, g1) after optional deprotection of the hydroxyl or the amino represented by $R'_2$ or optional conversion of $R'_2$ to $R_2$, the product of formula (I) obtained is optionally converted to one of its salts.

In step $c_1$) the compound 9a is advantageously methanesulfonyl chloride and therefore, in the compound 14 of step $d_1$), W is advantageously a methyl group.

The O-protecting groups optionally used to obtain a compound of formula (I) in which $R_2$ represents a hydroxyl are conventional O-protecting groups well known to persons skilled in the art as defined above for E.

The N-protecting groups optionally used to obtain a compound of formula (I) in which $R_2$ represents an amino are conventional N-protecting groups well known to persons skilled in the art such as for example the trityl, methoxytrityl, tert-butoxycarbonyl or benzyloxycarbonyl group.

In particular, when an acetyl group is used as O-protecting group, the compound of formula (I) obtained represents the final product in which $R_2$ represents an acetoxy or when a tert-butoxycarbonyl group is used as N-protecting group, the compound of formula (I) obtained represents the final product in which $R_2$ represents a tert-butoxycarbonylamino.

Particularly advantageous operating conditions of the above steps are hereinafter given and illustrated by the Examples.

In stage a), as functional derivative of the acid 3, the acid itself is used, or alternatively one of the functional derivatives which normally react with amines, for example an anhydride, a mixed anhydride, the acid chloride, or an activated ester such as paranitrophenyl ester.

When the acid of formula a itself is used, the procedure is carried out in the presence of a coupling agent used in peptide chemistry such as 1,3-dicyclohexyl-carbodiimide or benzotriazol-1-yloxytris(dimethylamino)-phosphonium hexafluorophosphate in the presence of a base such as triethylamine or N,N-diisopropylethylamine, in an inert solvent such as dichloromethane or N,N-dimethylformamide at a temperature of between 0° C. and room temperature.

When an acid chloride is used, the reaction is carried out in an inert solvent such as dichloromethane or benzene, in the presence of a base such as triethylamine or N-methylmorpholine and at a temperature between −60° C. and room temperature.

When a halogenated derivative of formula 4 is used, the reaction is carried out in an inert solvent such as tetrahydrofuran, N,N-dimethylformamide or dimethyl sulfoxide in the presence of a base such as potassium tert-butoxide, sodium hydride or lithium diisopropylamide and at a temperature between 0° C. and 80° C.

When a chloroformate of formula 5 is used, the reaction is carried out in an inert solvent such as dichloromethane, in the presence of a base such as triethylamine and at a temperature between 0° C. and room temperature.

When an isocyanate of formula 6 is used, the reaction is carried out in an inert solvent such as dichloromethane or benzene and at a temperature between −70° C. and room temperature.

When a carbamoyl chloride of formula 7 is used, the reaction is carried out in an inert solvent such as toluene or 1,2-dichloroethane, at a temperature between 0° C. and 110° C. and in the presence of a base such as s triethylamine.

When a benzenesulfonyl chloride of formula 7a is used, the reaction is carried out in an inert solvent such as dichloromethane, in the presence of a base such as triethylamine and at a temperature between −20° C. and room temperature.

The compound of formula 8 thus obtained is optionally deprotected at stage b) according to methods known to persons skilled in the art. For example, when E represents a tetrahydropyran-2-yloxy group, the deprotection is carried out by acid hydrolysis using hydrochloric acid in a solvent such as ether, methanol, or the mixture of these solvents, or using pyridinium p-toluenesulfonate in a solvent such as methanol or alternatively, using an Amberlyst® resin in a solvent such as methanol. The reaction is carried out at a temperature between room temperature and the reflux temperature of the solvent. When E represents a benzoyloxy group or a $(C_1–C_4)$alkylcarbonyloxy group, the deprotection is carried out by hydrolysis in alkaline medium using for example an alkali metal hydroxide such as sodium hydroxide, potassium hydroxide or lithium hydroxide, in an inert solvent such as water, methanol, dioxane or a mixture of these solvents, at a temperature between 0° C. and the reflux temperature of the solvent.

At stage c), the reaction of the alcohol of formula 9 with a sulfonyl chloride of formula 9a is preferably carried out in the presence of a base such as triethylamine, pyridine, N,N-diisopropylethylamine or N-methylmorpholine, in an inert solvent such as dichloromethane, benzene or toluene, at a temperature between −20° C. and the reflux temperature of the solvent.

When a compound of formula 10 is reacted with a compound of formula 11 (stage d), the reaction is preferably carried out in an inert solvent such as N,N-dimethylformamide, acetonitrile, methylene chloride, toluene or isopropanol and in the presence or in the absence of a base. When a base is used, it is chosen from organic bases such as triethylamine, N,N-diisopropylethylamine or N-methyl-morpholine or from alkali metal carbonates or bicarbonates such as potassium carbonate, sodium carbonate or sodium bicarbonate. In the absence of a base, the reaction is carried out using an excess of the compound of formula 11 and optionally in the presence of an alkali metal iodide such as potassium iodide or sodium iodide. The reaction is carried out at a temperature between room temperature and 100° C.

The products of formula (I) thus obtained are either isolated in the form of a free base or a salt, according to conventional techniques.

When the compound of formula (I) is obtained in the form of a free base, the salification is carried out by treating with the chosen acid in an organic solvent. By treating the free base, dissolved for example in an ether such as diethyl ether or in an alcohol such as propan-2-ol or in acetone, with a solution of the chosen acid in the same solvent, the corresponding salt is obtained which is isolated according to conventional techniques.

Thus, the hydrochloride, hydrobromide, sulfate, hydrogen sulfate, dihydrogen phosphate, methanesulfonate, oxalate, maleate, fumarate, naphthalene-2-sulfonate, benzenesulfonate are for example prepared.

At the end of the reaction, the compounds of formula (I) can be isolated in the form of one of their salts, for example the hydrochloride or the oxalate; in this case, if necessary, the free base can be prepared by neutralizing the said salt with an inorganic or organic base, such as sodium hydroxide or triethylamine or with an alkali metal carbonate or bicarbonate, such as sodium or potassium carbonate or bicarbonate.

The substituted piperidines of formula 11 are known or prepared by known methods.

The compounds of formula 11 are generally prepared in a form protected on the piperidine nitrogen; they make it possible to obtain, by a deprotection step, the compounds of formula 11 themselves. For example, when Ar is a pyrid-2-yl, 2-bromopyridine is reacted with N-benzyl-4-piperidone in a solvent in the presence of buytllithium in order to prepare N-benzyl-4-hydroxy-4-pyrid-2-ylpiperidine, and then by deprotection in a basic medium 4-hydroxy-4-pyrid-2-ylpiperidine.

The compounds of formula 11 in which $R'_2$ represents a hydroxyl and which carry a protecting group on the piperidine nitrogen can be subjected to a Ritter reaction by the action of acetonitrile in order to prepare the compounds of formula 11 in which $R'_2$ is an acetamido according to the procedure described in Patent Application EP-474561. By hydrolysis in acidic medium, the compounds of formula 11 in which $R'_2$ is an amino are then prepared. Optionally, it is possible to carry out the substitution of the amino group by a group $R_3=(C_1-C_4)$alkyl. The compounds of formula 11 in which $R'_2$ represents an —$NR_3COR_4$— group in which $R_3$ represents a hydrogen or a $(C_1-C_4)$alkyl and $R_4$ represents a hydrogen or respectively a $(C_1-C_7)$alkyl, a phenyl, a benzyl, a pyridyl or a $(C_3-C_7)$cycloalkyl which is optionally substituted, are obtained by the action of formic acid in acetic anhydride or respectively of the appropriate anhydride $(R_4CO)_2O$ or of an appropriate acid chloride $R_4COCl$ in the presence of a base such as triethylamine, on a compound of formula 11 in which $R'_2$ represents an —$NHR_3$ group.

In particular, a compound of formula 11 in which $R'_2$ represents an —$NR_3COR_4$ group in which $R_4$ represents an ethyl radical can be prepared by hydrogenation, in the presence of a catalyst such as palladium on charcoal, of a compound of formula 11 in which $R'_2$ represents an acryloylamino or acryloyl-N-$(C_1-C_4)$alkylamino group.

The compounds of formula 11 in which $R'_2$ is the —$NR_3COOR_8$ group are prepared by the action of a chloroformate $ClCOOR_8$. The compounds of formula 11 in which $R'_2$ is the —$NR_3SO_2R_9$ group are prepared by the action of a sulfonyl chloride $ClSO_2R_9$. The compounds of formula 11 in which $R'_2$ is the —$NR_3CONR_{10}R_{12}$ group with $R_{10}$=H are prepared by the action of an isocyanate $R_{12}N=C=O$. The compounds of formula 11 in which $R'_2$ is the —$NR_3CONR_{10}R_{12}$ group are prepared by the action of a carbamoyl chloride $R_{12}R_{10}NCOCl$.

A compound of formula 11 in which $R'_2$ is an —$NR_3CONR_{10}R_{12}$ group can also be obtained by reacting a compound $HNR_{10}R_{12}$ with a compound of formula 11 in which $R'_2$ is an —$NR_3COOR_8$ group with $R_8$=phenyl.

It goes without saying that the reactions leading to the compounds of formula 11 where $R'_2$ is —$NHR_3$, —$NR_3COOR_8$, —$NR_3SO_2R_9$ or —$NR_3CONR_{10}R_{12}$ are directly transposable to the preparation of the compounds 11 where $R'_2$ is —$CH_2NHR_3$, —$CH_2NR_3COOOR_8$, —$CH_2NR_3SO_2R_9$ or —$CH_2NR_3CONR_{10}R_{12}$.

A compound of formula 11 in which $R'_2$ is an —$NR_6R_7$ group in which $R_6$ and $R_7$ together with the nitrogen to which they are attached constitute a heterocycle, is prepared according to the method described in Tetrahedron Letters, 1988, 29, 29 (52), 6827.

A compound of formula 11 in which $R'_2$ is a hydroxymethyl is prepared by reducing a compound of formula 11 in which $R'_2$ is a methoxycarbonyl by the action of a reducing agent such as lithium aluminum hydride. The compounds of formula 11 in which $R'_2$ is a $(C_2-C_7)$acyloxymethyl are obtained by the action of a $(C_2-C_7)$ acid chloride on a compound of formula 11 in which $R'_2$ is a hydroxymethyl; the compound of formula 11 in which $R'_2$ is a formyloxymethyl is obtained by the action of formic acid. The compounds of formula 11 in which $R'_2$ is a $(C_1-C_7)$ alkylaminocarbonyloxymethyl are obtained by the action of a carbamoyl chloride $(C_1-C_7)$alkylNHCOCl on a compound of formula 11 in which $R'_2$ is a hydroxymethyl.

A compound of formula 11 in which Ar and $R'_2$ together with the carbon atom to which they are attached constitute a group of formula:

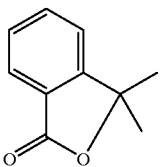

is prepared according to the method described in J. Heteroc. Chem., 1969, 6, 475.

The compounds of formula 11 in which $R'_2$ is a $(C_2-C_7)$ acyloxy are obtained by the action of a $(C_2-C_7)$ acid chloride on the compounds of formula 11 in which $R'_2$ represents a hydroxyl; the compounds of formula 11 in which $R'_2$ is a formyloxy are obtained by the action of formic acid.

To prepare a compound of formula 11 in which $R'_2$ is $R_4CONR_3$—, with $R_3$ and $R_4$ together representing a —$(CH_2)_3$— or —$(CH_2)_4$— group, the procedure is carried out according to J. Med. Chem., 1985, 28, 46–50.

The conversion of a substituent $R_2$=cyano to a substituent $R_2$=aminomethyl can be carried out by catalytic hydrogenation either on a compound of formula 11, or on a compound of formula (I). Compounds according to the invention, variously substituted on the aminomethyl nitrogen, are then prepared by appropriate reactions.

The above methods are well known and are illustrated by the Preparations below, preceding the EXAMPLES. These preparations constitute adaptations of the methods described in EP-A-0,428,434, EP-A-0,474,561, EP-A-0,512,901 or in the following publications.

J. Heterocyclic. Chem., 1986, 23, 73–75

J. Chem. Soc., 1950, 1469

J. Chem. Soc., 1945, 917

J. Pharmaceutical. Sci., 1972, 61, 1316–1317

J. Org. Chem. 1957, 22, 1484–1489.

Thus for example, to prepare a compound of formula 11 in which $R'_2$ represents an —$NR_6R_7$ group in which $R_6$ represents a hydrogen and $R_7$ represents a $(C_1-C_7)$alkyl, or respectively a $(C_3-C_7)$cycloalkylmethyl or a benzyl, a reduction can be carried out of a is compound of formula 11 in which $R'_2$ represents an —$NR_3COR_4$ group in which $R_3$ represents hydrogen and $R_4$ represents a hydrogen or a $(C_1-C_6)$alkyl, or respectively a $(C_3-C_7)$cycloalkyl or a phenyl. The reaction is carried out by means of a reducing agent such as lithium aluminum hydride in a solvent such as tetrahydrofuran at the reflux temperature of the solvent.

By an identical reaction, the compounds of formula 11 in which $R'_2$ represents an —$NR_6R_7$ group in which $R_6$ represents a $(C_1-C_4)$alkyl and $R_7$ represents a $(C_1-C_7)$alkyl, or respectively a $(C_3-C_7)$cycloalkylmethyl or a benzyl, can be prepared from a compound of formula 11 in which $R'_2$ represents an —$NR_3COR_4$ group in which $R_3$ represents a $(C_1-C_4)$alkyl and $R_4$ represents a hydrogen or a $(C_1-C_6)$ alkyl, or respectively a $(C_3-C_7)$cycloalkyl or a phenyl. Likewise, the compounds of formula 11 in which $R'_2$ represents an —$NR_6R_7$ group in which $R_6$ represents a $(C_5-C_7)$ alkyl can be prepared.

Likewise, the compounds of formula 11 in which $R'_2$ represents a —$CH_2NR_{13}R_{14}$ group in which $R_{13}$ represents a hydrogen or a $(C_1-C_4)$alkyl and $R_{14}$ represents a $(C_1-C_7)$ alkyl, a $(C_3-C_7)$cycloalkylmethyl or a benzyl, can be prepared from a compound of formula 11 in which $R'_2$ represents a —$CH_2NR_3COR_4$ group in which $R_3$ represents a hydrogen or a $(C_1-C_4)$alkyl and $R_4$ represents a hydrogen, a $(C_1-C_6)$alkyl, a $(C_3-C_7)$cycloalkyl or a phenyl. Likewise, the compounds of formula 11 in which $R'_2$ represents a —$CH_2NR_{13}R_{14}$ group in which $R_{13}$ represents a $(C_5-C_7)$ alkyl can be prepared.

The conversion of a substituent $R_2$=hydroxyl or hydroxymethyl to a substituent $R_2$=$(C_1-C_7)$acyloxy or $(C_1-C_7)$acyloxymethyl can be carried out either on a compound of formula 11 or on a compound of formula (I).

Optionally, the conversions of the $R_2$ group from $R'_2$=hydroxyl or amino can be carried out on a compound of formula 15.

The piperidine derivatives of formula:

(V)

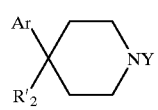

in which

Ar is as defined above for (I);

$R'_2$ represents an —$NR_3COR_4$ group with $R_3$ and $R_4$ as defined above for (I), provided that when $R_3$ is hydrogen, $R_4$ is other than methyl;

Y represents hydrogen or a protecting group such as a tert-butoxycarbonyl, a trityl or a benzyl; as well as their salts where appropriate are new and constitute a subsequent aspect of the present invention.

Advantageous products amongst these compounds are those of formula (V) in which Ar is phenyl, $R'_2$ is an —$NR_3COR_4$ group, $R_3$ being methyl and $R_4$ being $(C_1-C_7)$ alkyl, and Y is hydrogen or an N-protecting group, as well as their possible salts.

Particularly preferred according to the invention are the compounds of formula (V), in which Ar is phenyl, $R'_2$ is an —$NR_3COR_4$ group, $R_3$ and $R_4$ both being methyl, and Y is hydrogen or a protecting group, in particular tert-butoxycarbonyl, trityl or benzyl, as well as their possible salts.

The compounds of formula 1 in which E represents a hydroxyl are prepared by known methods. The following SCHEME 1 summarizes one of these methods for the compounds of formula 1'.

SCHEME 1

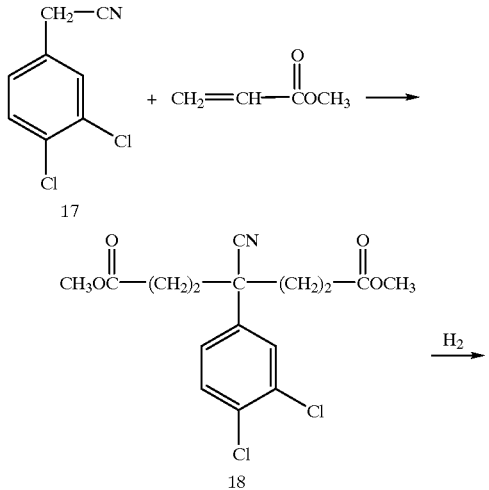

-continued

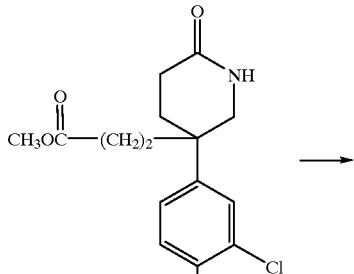

19

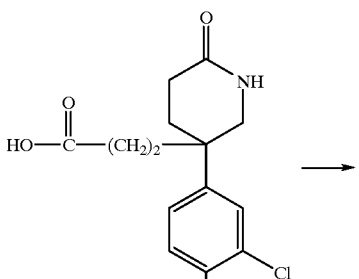

20

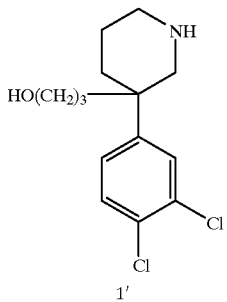

1'

Compounds 3, 4, 5, 6, 7, 7a are known or prepared by known methods.

These compounds can be used in labeled form, for example with tritium, or with radioactive iodine, in order to prepare compounds (I) according to the invention which are labeled.

In this case, the procedure is carried out starting with a compound a, 3, 4, 5, 6, 7, 7a in which the radical Z is substituted by an iodine atom, then this iodine atom is exchanged with a tritium or a radioactive iodine atom in order to prepare a labeled compound 3*, 4*, 5*, 6*, 7* and 7*a which makes it possible to prepare a labeled compound of formula (I*), more particularly a labeled compound of formula (IV*).

The alcohol (1') obtained according to scheme 1 is racemic. The separation of its optical isomers can be optionally carried out by known methods, for example by chromatography or recrystallization, then the corresponding optically pure mesylate can be prepared and the compounds according to the invention can thus be prepared in optically pure form.

The alcohol (1'), which constitutes the key intermediate in the synthesis of the compounds of formula (IV), which are particularly preferred as potent and selective antagonists of the human NK₃ receptor, is a new compound. The racemic form of this alcohol, the two (+) and (−) enantiomers and the salts of these compounds are therefore another aspect of the present invention, the isomer (+) and its acid addition salts being particularly preferred.

According to another aspect, the subject of the present invention is the use of a nonpeptide compound which is a specific antagonist of the human NK₃ receptor having a very high affinity for said receptor, for the preparation of medicinal products which are useful in the treatment of any pathology in which neurokinin B is involved, in particular for the preparation of medicinal products intended to combat psychiatric diseases, diseases of psychosomatic origin, hypertension, pathologies linked to NK₃-dependent neuromodulation or neurotransmission disorders.

The invention relates in particular to the use of a compound of formula (I'):

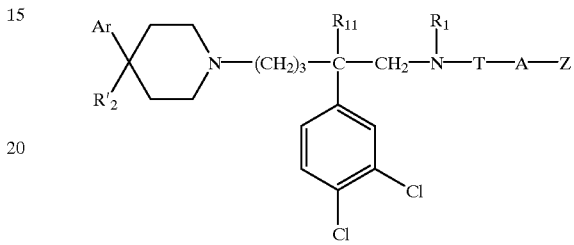

(I')

in which:

Ar represents a pyrid-2-yl or a phenyl which is unsubstituted or substituted by a halogen, a methyl or a (C₁–C₄) alkoxy;

R₁ represents a methyl group;

R₁₁ represents hydrogen;

or R₁ and R₁₁ together represent a —(CH₂)₃— group;

R₂ represents a hydroxyl; a (C₁–C₇)alkoxy; a (C₁–C₇) acyloxy; a cyano; an —NR₆R₇ group; an —NR₃COR₄ group; an —NR₃COOR₈ group; an —NR₃SO₂R₉ group; an —NR₃CONR₁₀R₁₂ group; a (C₁–C₇)acyl group; a (C₁–C₇)alkoxycarbonyl; a —CONR₁₀R₁₂ group; a —CH₂OH group; a (C₁–C₇)alkoxymethyl; a (C₁–C₇)acyloxymethyl; a (C₁–C₇) alkylaminocarbonyloxymethyl; a —CH₂NR₁₃R₁₄ group; a —CH₂NR₃COR₄ group; a —CH₂NR₃COORB group; a —CH₂NR₃SO₂R₉ group; a —CH₂NR₃CONR₁₀R₁₂ group; or R₂ constitutes a double bond between the carbon atom to which it is attached and the adjacent carbon atom of the piperidine ring;

or Ar and R₂, together with the carbon atom to which they are attached, constitute a group of formula:

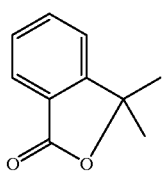

R₃ represents a hydrogen or a (C₁–C₄)alkyl;

R₄ represents a hydrogen, a (C₁–C₇)alkyl, a phenyl, a benzyl, a pyridyl or a (C₃–C₇)cycloalkyl which is unsubstituted or substituted by one or more methyls;

or R₃ and R₄ together represent a —(CH₂)ₙ— group;

n is 3 or 4;

T represents a methylene, a carbonyl, a —COO— group, a —CONR₅— group;

A represents a direct bond, a methylene, an ethylene, a propylene, a vinylene;

or —T—A— represents the —SO$_2$— group

Z represents a phenyl which is unsubstituted or substituted one or several times by a halogen, a (C$_1$–C$_4$)alkyl, a (C$_1$–C$_4$)alkoxy, a nitro;

R$_5$ represents a hydrogen or a (C$_1$–C$_4$)alkyl;

R$_6$ and R$_7$ each represent independently a hydrogen or a (C$_1$–C$_7$)alkyl; R$_7$ can furthermore represent a (C$_3$–C$_7$) cycloalkylmethyl, a benzyl or a phenyl; or R$_6$ and R$_7$, together with the nitrogen atom to which they are attached, constitute a heterocycle chosen from azetidine, pyrrolidine, piperidine, morpholine, thiomorpholine or perhydroazepine;

R$_8$ represents a (C$_1$–C$_7$)alkyl or a phenyl;

R$_9$ represents a (C$_1$–C$_7$)alkyl; an amino which is free or substituted by one or two (C$_1$–C$_7$)alkyls; a phenyl which is unsubstituted or substituted once or several times by a substituent chosen from: a halogen atom, a (C$_1$–C$_7$)alkyl, a trifluoromethyl, a hydroxyl, a (C$_1$–C$_7$) alkoxy, a carboxyl, a (C$_1$–C$_7$)alkoxycarbonyl, a (C$_1$–C$_7$)alkylcarbonyloxy, a cyano, a nitro, an amino which is free or substituted by one or two (C$_1$–C$_7$) alkyls, said substituents being identical or different;

R$_{10}$ and R$_{12}$ each represent independently a hydrogen or a (C$_1$–C$_7$)alkyl; R$_{12}$ may furthermore represent a (C$_3$–C$_7$)cycloalkyl, a (C$_3$–C$_7$)cycloalkylmethyl, a hydroxyl, a (C$_1$–C$_4$)alkoxy, a benzyl or a phenyl; or R$_{10}$ and R$_{12}$, together with the nitrogen atom to which they are attached, constitute a heterocycle chosen from azetidine, pyrrolidine, piperidine, morpholine, thiomorpholine or perhydroazepine;

R$_{13}$ and R$_{14}$ each represent independently a hydrogen or a (C$_1$–C$_7$)alkyl; R$_{14}$ may furthermore represent a (C$_3$–C$_7$)cycloalkylmethyl or a benzyl;

or of its pharmaceutically acceptable salts, for the preparation of medicinal products as defined above and advantageously for the preparation of medicinal products which are useful for treating hypertension.

The affinity of the compounds of formula (I') for the tachykinin receptors was evaluated in vitro by several biochemical assays using radioligands:

1) The binding of [$^{125}$I]BH-SP (substance P labeled with iodine 125 with the aid of the Bolton-Hunter reagent) to the NK$_1$ receptors of rat cortex, of guinea pig ileum and of human lymphoblastic cells.

2) The binding of [$^{125}$I]His-NK$_A$ to the NK$_2$ receptors of rat duodenum or of guinea pig ileum.

3) The binding of [$^{125}$I]His[MePhe$^7$]NK$_B$ to the NK$_3$ receptors of rat cerebral cortex, of guinea pig cerebral cortex and of gerbil cerebral cortex as well as to the cloned human NK$_3$ receptors expressed by CHO cells (Buell et al., FEBS Letters, 1992, 299, 90–95).

The assays were carried out according to X. Emonds-Alt et al. (Eur. J. Pharmacol., 1993, 250, 403–413).

The compounds according to the invention strongly inhibit the binding of [$^{125}$I]His[MePhe$^7$]NK$_B$ to the NK$_3$ receptors of guinea pig and gerbil cerebral cortex as well as to cloned human NK$_3$ receptors; the inhibition constant Ki is generally less than 5·10$^{-9}$M. For the same compounds, it was observed that the inhibition constant (Ki) for the NK$_3$ receptors of rat cerebral cortex is greater than 10$^{-7}$M and that the inhibition constant (Ki) for the NK$_2$ receptor of rat duodenum and the NK$_1$ receptors of rat cortex is generally greater than or equal to 10$^{-7}$M.

By way of comparison, the inhibition constants for the various receptors for compound A were measured according to the procedures described above. The antagonism of the eledoisin binding described in Application EP 512901 corresponds to the inhibition constant of the rat NK$_3$ receptor:

Ki=10$^{-7}$M

For the human NK$_3$ receptor, the inhibition constant of compound A is Ki=1·10$^{-9}$M.

For the rat duodenum NK$_2$ receptor, the inhibition constant of compound A is Ki=1·10$^{-10}$M.

Thus, compound A is not selective for the human NK$_3$ receptor contrary to what is observed for the compounds of formula (I) according to the present invention.

The N-methyl-N-(2-[3,4-dichlorophenyl)-5-(4-hydroxy-4-phenylpiperidin-1-yl)pentyl]benzamide hydrochloride described in Example 22 of Application EP 474561 belongs to the family of compounds (I') according to the present invention; its inhibition constants show the high specificity and the high affinity of this compound for the human NK$_3$ receptor:

human NK$_3$ receptor, Ki=5·10$^{-9}$M rat duodenum NK$_2$ receptor, Ki=5·10$^{-7}$M rat cortex NK$_1$ receptor, Ki=5·10$^{-7}$M.

The compounds according to the present invention were also evaluated in vivo on two animal models.

In gerbils, a rotating behavior is induced by intrastriatal administration of an NK$_3$ receptor-specific agonist: senktide; it was observed that a unilateral application of senktide in the gerbil striatum leads to strong contralateral rotations which are inhibited by the compounds according to the invention when administered either intraperitoneally or orally.

This result shows that the compounds according to the invention cross the hematomeningeal barrier and that they are capable of blocking, in the central nervous system, the action specific to the NK$_3$ receptors. They can thus be used for the treatment of any NK$_B$-dependent central pathology, such as psychiatric diseases, or of any pathology mediated, at the central level, by the NK$_3$ receptor, such as psychosomatic diseases.

In guinea pigs, an intravenous or intracerebroventricular injection of senktide induces a hypertension which is suppressed by the oral or intravenous administration of the compounds according to the invention.

This result shows that the compounds according to the invention act at the cardiovascular level and that they are capable of blocking the action specific to the NK$_3$ receptors at this level, especially hypertension (Nakayama et al., Brain Res. 1992, 595 339–342, Takano and Kamiya, Asia Pacific, J. Pharmacol., 1991, 6, 341–346, Saigo et al., Neuroscience Letters, 1993, 159, 187–190).

In these tests, the compounds according to the invention are active at doses ranging from 0.1 mg to 3 mg per kg orally, intravenously or intraperitoneally.

The compounds which are useful for preparing medicinal products according to the invention are generally administered as dosage units. Preferred dosage units are preferably formulated in pharmaceutical compositions in which the active ingredient is mixed with a pharmaceutical excipient.

According to another of its aspects, the present invention relates to pharmaceutical compositions containing, as active ingredient, a compound of formula (I), advantageously of formula (II) or (III), preferably of formula (IV) having a very high affinity for the human NK$_3$ receptor, characterized by an inhibition constant Ki of less than 5·10$^{-9}$M in ligand binding studies.

The compounds of formula (I) and their pharmaceutically acceptable salts can be used at daily doses of 0.01 to 100 mg per kilo of body weight of the mammal to be treated, preferably at daily doses of 0.1 to 50 mg/kg. In humans, the dose may range preferably from 0.5 to 4000 mg per day, more particularly from 2.5 to 1000 mg according to the age of the subject to be treated or the type of treatment: prophylactic or curative.

The diseases for the treatment of which the compounds and their pharmaceutically acceptable salts can be used are for example diseases associated with a dysfunction of the dopaminergic systems such as schizophrenia, Parkinson's disease, diseases associated with a dysfunction of the noradrenergic systems such as anxiety, vigilance disorders as well as epileptic diseases of any form and in particular Grand Mal, dementia, neurodegenerative diseases, and peripheral diseases in which the participation of the central nervous system and/or the peripheral nervous system occurs via neurokinin B acting as central neurotransmitter or neuromodulator, such as pain, migraine, acute or chronic inflammation, cardiovascular disorders, in particular hypertension, cardiac insufficiency, and rhythm disorders, respiratory disorders (asthma, rhinitis, cough, bronchitis, allergies, hypersensitivity), disorders of the gastrointestinal system such as esophageal ulcer, colitis, stress-related disorders, irritable bowel syndrome (IBS), inflammatory bowel diseases (IBD), acidic secretion, disorders of the urinary system (incontinence, neurogenic bladder), diseases of the immune system (rheumatoid arthritis), and more generally any neurokinin B-dependent pathology.

In the pharmaceutical compositions of the present invention for oral, sublingual, inhaled, subcutaneous, intramuscular, intravenous, transdermal, local or rectal administration, the active ingredients can be administered in unit forms for administration, mixed with conventional pharmaceutical carriers, to animals and to humans. The appropriate unit forms for administration comprise the oral forms such as tablets, gelatin capsules, powders, granules and oral solutions or suspensions, the forms for sublingual and buccal administration, the forms for subcutaneous, intramuscular, intravenous, intranasal or intraocular administration and the forms for rectal administration.

When a solid composition is prepared in the form of tablets, the main active ingredient is mixed with a pharmaceutical vehicle such as silica, gelatin, starch, lactose, magnesium stearate, talc, gum arabic and the like. The tablets can be coated with sucrose, with various polymers or with other appropriate materials or alternatively they can be treated so that they have a prolonged or delayed activity and that they release a predetermined quantity of active ingredient continuously.

A gelatin capsule preparation is obtained by mixing the active ingredient with a diluent such as a glycol or a glycerol ester and incorporating the mixture obtained into soft or hard gelatin capsules.

A preparation in the form of syrup or elixir may contain the active ingredient together with a sweetener which is preferably calory free, methylparaben and propylparaben as antiseptic, as well as a taste enhancing agent and an appropriate coloring.

Water-dispersible powders or granules may contain the active ingredient mixed with dispersing agents or wetting agents, or suspending agents, such as polyvinylpyrrolidone, as well as with sweeteners or taste correctors.

For rectal administration, suppositories are used which are prepared with binders melting at the rectal temperature, for example cocoa butter or polyethylene glycols.

For a parenteral, intranasal or intraocular administration, aqueous suspensions, isotonic saline solutions or injectable solutions containing pharmacologically compatible dispersing agents and/or wetting agents, for example propylene glycol or butylene glycol, are used.

For administration by inhalation, an aerosol is used containing, in addition, for example sorbitan trioleate or oleic acid as well as trichlorofluoromethane, dichlorofluoromethane, dichlorotetrafluoroethane or any other biologically compatible propelling gas; a system containing the active ingredient, alone or combined with an excipient, in the form of a powder can also be used.

The active ingredient may also be present in the form of a complex with a cyclodextrin, for example α-, β-, γ-cyclodextrin, 2-hydroxypropyl-β-cyclodextrin, methyl-β-cyclodextrin.

The active ingredient may also be formulated in the form of microcapsules, optionally with one or more carriers or additives.

In each dosage unit, the active ingredient of formula (I) is present in quantities adapted to the expected daily doses. In general, each dosage unit is suitably adjusted according to the dosage and the type of administration intended, for example tablets, gelatin capsules and the like, sachets, ampoules, syrups and the like, drops, so that such a dosage unit contains from 0.5 to 1000 mg of active ingredient, preferably from 2.5 to 250 mg to be administered once to four times per day.

The abovementioned compositions may also contain other active products which are useful for the desired therapy, such as for example bronchodilators, anti-coughs or antihistaminics.

By virtue of their very high affinity for the human $NK_3$ receptor and their high selectivity, it will be possible to use the compounds according to the invention in radiolabeled form as laboratory reagents.

For example they make it possible to carry out the characterization, identification and localization of the human $NK_3$ receptor in tissue sections, or of the $NK_3$ receptor in the whole animal by autoradiography.

The compounds according to the invention also make it possible to carry out the sorting or screening of molecules according to their affinity for the human $NK_3$ receptor. In this case, the procedure is carried out by a reaction for displacing the radiolabeled ligand, which is the subject of the present invention, from its human $NK_3$ receptor.

In the examples which follow, the following abbreviations are used:
RT: room temperature
m.p.: melting point
TEA: triethylamine
Pd/C: 10% palladium on charcoal
DCM: dichloromethane
THF: tetrahydrofuran
DBU: 1,8-diazabicyclo[5.4.0]undec-7-ene
DMAP: 4-dimethylaminopyridine
AcOEt: ethyl acetate
MeOH: methanol
HPLC: high-performance liquid chromatography
Me: methyl
iPr: isopropyl
Bu: n-butyl
HCl: hydrochloric acid
$(Boc)_2O$: di-tert-butyl dicarbonate
Boc=tert-butoxycarbonyl
BOP: benzotriazol-1-yloxy-tris(dimethylamino)-phosphonium hexafluorophosphate NaCl: sodium chloride
MgSO$_4$: magnesium sulfate
Na$_2$SO$_4$: sodium sulfate
LiAlH$_4$: lithium aluminum hydride
NaOH: sodium hydroxide
NH$_4$Cl: ammonium chloride
ether: diethyl ether
isoether: diisopropyl ether
Et: ethyl
C$_6$H$_5$: phenyl
K$_2$CO$_3$: potassium carbonate
hydrochloric ether: saturated solution of HCl in ether
silica H: silica gel 60 H marketed by Merck (DARMSTADT)
NMR: nuclear magnetic resonance
s: singlet
bs: broad singlet
d: doublet
t: triplet
m: unresolved complex
mt: multiplet
st: split triplet
ss: split singlet

PREPARATIONS

Preparation 1.1

4-Phenyl-4-pivaloylaminopiperidine

A) 1-Benzyl-4-hydroxy-4-phenylpiperidine

This compound is prepared by the action of phenyllithium on 1-benzylpiperidin-4-one.

B) 4-Acetamido-1-benzyl-4-phenylpiperidine.

This compound is obtained according to the Ritter reaction by the addition of acetonitrile onto the compound prepared in stage A.

C) 4-Amino-1-benzyl-4-phenylpiperidine dihydrochloride.

The compound prepared in stage B is hydrolyzed by refluxing for 3 hours in 6N HCl. After evaporation to dryness, the residue is dissolved in methanol, crystallized by addition of acetone, filtered and dried to give the expected compound.

D) 1-Benzyl-4-phenyl-4-pivaloylaminopiperidine.

70 g of the compound prepared in the preceding stage are dissolved in 150 ml of dioxane, 85 ml of TEA are added followed by 45 g of pivaloyl chloride. After stirring for 2 hours at 60° C., the mixture is evaporated, taken up in DCM, washed with dilute sodium hydroxide, with a solution of NaCl and then dried over MgSO$_4$ and evaporated. The residue is chromatographed on silica, eluting with DCM. 43 g of the expected product are obtained in the form of an oil.

E) 4-Phenyl-4-pivaloylaminopiperidine.

13 g of the compound obtained in the preceding stage are dissolved in 20 ml of 95% ethanol; 1.5 g of Pd/C are added and the mixture is hydrogenated for 24 hours at room temperature, at atmospheric pressure, filtered, evaporated so as to obtain an oil which crystallizes giving 8 g of expected product.

Preparation 1.2

4-Phenyl-4-(pivaloyl-N-methylamino)piperidine

A) 1-Benzyl-4-(N-tert-butoxycarbonylamino)-4-phenylpiperidine.

A solution of 12 g of (Boc)$_2$O in 50 ml of dioxane is added dropwise to a solution of 14.5 g of 4-amino-1-benzyl-4-phenylpiperidine dihydrochloride obtained in stage C of Preparation 1.1, 12 ml of TEA in 100 ml of dioxane, and the mixture is heated for 18 hours at 50° C. The reaction mixture is concentrated under vacuum, the residue extracted with AcOEt, washed with a buffer solution pH=2, with a 1N solution of NaOH, dried over MgSO$_4$ and the solvent evaporated under vacuum. 13 g of the expected product are obtained after crystallization from the ether/heptane mixture.

B) 4-(N-tert-butoxycarbonylamino)-4-phenylpiperidine.

A mixture of 13 g of the compound obtained in the preceding stage, 1.5 g of 10% palladium on charcoal in 300 ml of 95% EtOH is hydrogenated for 72 hours at RT and at atmospheric pressure. The catalyst is filtered on Celite® and the filtrate evaporated under vacuum. 9.7 g of the expected product are obtained.

C) 4(N-tert-butoxycarbonylamino)-4-phenyl-1-tritylpiperidine.

13.25 g of the compound obtained in the preceding stage and 5 g of TEA are dissolved in 150 ml of DCM at 0° C., under nitrogen. 13.4 g of trityl chloride are added dropwise and the mixture is kept stirring for 1 hour. The reaction mixture is evaporated, taken up in ether, washed with water, with a buffer solution at pH 2, a solution of NaCl, and then dried over MgSO$_4$ and evaporated. 23 g of the expected product are obtained in the form of an oil.

D) 4(N-Methylamino)-4-phenyl-1-tritylpiperidine.

A suspension of 5 g of LiAlH$_4$ in 100 ml of THF is heated to 60° C., under nitrogen, and a solution of 23 g of the compound obtained in the preceding stage in 100 ml of THF is added dropwise. After refluxing for 2 hours, the reaction mixture is hydrolyzed with 25 ml of water, filtered, evaporated. 17 g of the expected product are obtained, which product crystallizes from hot methanol, m.p.=125° C.

E) 4-(Pivaloyl-N-methylamino)-4-phenyl-1-tritylpiperidine.

2.6 g of the compound obtained in the preceding stage are dissolved in 15 ml of pyridine, 500 mg of DMAP and 4 ml of pivaloyl chloride are added. The mixture is allowed to react for 72 hours at 70° C. under nitrogen and then evaporated, dissolved in AcOEt, washed with water, a buffer solution at pH=2, a 5% solution of sodium hydroxide, a solution of NaCl, and then dried over MgSO$_4$. The residue is chromatographed on silica, eluting with a pentane/AcOEt mixture. The expected product (1.5 g) is obtained in the form of an oil.

F) 4-Phenyl-4-(Pivaloyl-N-methylamino)piperidine.

1.5 g of the product obtained in the preceding stage are dissolved in a mixture of 20 ml of formic acid and 20 ml of water. After stirring for 1 hour, the reaction mixture is filtered, the filtrate neutralized by the addition at cold temperature of a 40% solution of NaOH and then extracted 3 times with 50 ml of DCM; the resulting material is dried over MgSO$_4$ and evaporated. 700 mg of the expected product are obtained in the form of a pasty product, m.p.=50–55° C.

Preparation 1.3

4-(Acetyl-N-methylamino)-4-phenylpiperidine

A) 4-(Acetyl-N-methylamino)-4-phenyl-1-tritylpiperidine.

A solution of 2.8 g of the compound obtained in stage D of the Preparation 1.2 in 20 ml of DCM is cooled to 0° C., under nitrogen, and 1.5 ml of TEA are added, followed by 0.55 g of acetyl chloride. The mixture is kept stirring for 2 hours and the reaction mixture is concentrated under vacuum. The residue is taken up in AcOEt, washed with a buffer solution pH=2, with a 5% solution of NaOH, with a saturated solution of NaCl, dried over MgSO$_4$ and the solvent evaporated under vacuum. 3 g of the expected product are obtained.

B) 4-(Acetyl-N-methylamino)-4-phenylpiperidine

A solution of 3 g of the compound obtained in the preceding stage, 30 ml of formic acid in 15 ml of water is heated at 60° C. for 1 hour. 50 ml of water are added to the reaction mixture; it is filtered, the filtrate washed with ether, the aqueous phase alkalinized to pH>10 by addition of a concentrated solution of NaOH, extracted with DCM, dried over $MgSO_4$ and the solvent evaporated under vacuum. 1 g of the expected product is obtained in the form of an oil.

Preparation 1.4

4-[(Acetyl-N-methylamino)methyl]-4-phenylpiperidine p-toluenesulfonate

A) 4(Aminomethyl)-1-benzyl-4-phenylpiperidine.

A suspension of 2.8 g of lithium aluminum hydride in 50 ml of THF is cooled to 0° C. and a solution of 20 g of 1-benzyl-4-cyano-4-phenylpiperidine in 50 ml of THF is added dropwise. The mixture is kept stirring for 1 hour at RT and then heated at 40° C. for 1 hour. The reaction mixture is cooled on an ice bath, and 3 ml of water, 3 ml of a 4N solution of NaOH and 12 ml of water are added successively. The inorganic salts are filtered and the filtrate evaporated under vacuum. The residue is chromatographed on silica H, eluting with the gradient of the DCM/MeOH mixture from (100/3; v/v) to (100/10; v/v). 11 g of the expected product are obtained.

B) 1-Benzyl-4-[(N-formylamino)methyl]-4-phenylpiperidine.

25 ml of acetic anhydride are added, at RT and dropwise, to a mixture of 11 g of the compound obtained in the preceding stage in 76 ml of formic acid, then the mixture is kept stirring for 5 hours. The reaction mixture is concentrated under vacuum, the residue taken up in water, alkalinized to pH=14 by addition of concentrated NaOH, extracted with ether, washed with water, dried over $Na_2SO_4$ and the solvent evaporated under vacuum. 12 g of the expected product are obtained.

C) 1-Benzyl-4-[(N-methylamino)methyl]-4-phenylpiperidine.

A suspension of 3.9 g of lithium aluminum hydride in 50 ml of THF is heated to 40° C., a solution of 12 g of the compound obtained in the preceding stage in 50 ml of THF is added dropwise and the mixture ref luxed for 3 hours. After cooling on an ice bath, 4 ml of water, 4 ml of a 4N solution of NaOH and 12 ml of water are added successively. The inorganic salts are filtered and the filtrate concentrated under vacuum. The residue is extracted with ether, dried over $Na_2SO_4$ and the solvent evaporated under vacuum. 10 g of the expected product are obtained.

D) 4-[(Acetyl-N-methylamino)methyl]-1-benzyl-4-phenylpiperidine.

0.863 g of acetyl chloride is added to a solution of 3.3 g of the compound obtained in the preceding stage, 1.4 g of triethylamine in 50 ml of DCM, and the mixture is kept stirring for 2 hours at RT. The reaction mixture is concentrated under vacuum, the residue taken up in water, extracted with ether, washed with water, dried over $Na_2SO_4$ and the solvent evaporated. The residue is chromatographed on silica H, eluting with the DCM/MeOH mixture (100/3; v/v). 2.4 g of the expected product are obtained.

E) 4-[(acetyl-N-methylamino)methyl]-4-phenylpiperidine p-toluenesulfonate.

A mixture of 2.3 g of the compound obtained in the preceding stage, 1.2 g of p-toluenesulfonic acid monohydrate, 0.23 g of 10% palladium on charcoal and 100 ml of MeOH is hydrogenated at RT and at atmospheric pressure. The catalyst is filtered and the filtrate evaporated under vacuum. 2.7 g of the expected product are obtained.

Preparation 1.5

4-[(N'-Ethyl-N-methylureido)methyl]-4-phenylpiperidine

A) 1-Benzyl-4-[(N'-ethyl-N-methylureido)methyl]-4-phenylpiperidine

A solution of 0.71 g of ethyl isocyanate in 10 ml of DCM is added at RT to a solution of 2.7 g of the compound obtained in stage C of the PREPARATION 1.4 in 50 ml of DCM and the mixture is kept stirring for 1 hour. The reaction mixture is concentrated under vacuum and the residue chromatographed on silica H, eluting with the DCM/MeOH mixture (100/2.5; v/v). 1.7 g of the expected product are obtained.

B) 4-[(N'-Ethyl-N-methylureido)methyl]-4-phenylpiperidine.

A mixture of 1.7 g of the compound obtained in the preceding stage, 0.2 g of 10% palladium on charcoal and 50 ml of MeOH is hydrogenated at 40° C. and at atmospheric pressure. The catalyst is filtered and the filtrate evaporated under vacuum. 1.23 g of the expected product are obtained.

Preparation 1.6

4-[(N',N'-Diethyl-N-methylureido)methyl]-4-phenylpiperidine p-toluenesulfonate

A) 1-Benzyl-4-[(N',N'-diethyl-N-methylureido)methyl-4-phenylpiperidine.

1.92 g of N,N-diethylcarbamoyl chloride are added at RT to a solution of 4 g of the compound obtained in stage C of the PREPARATION 1.4, 1.55 g of triethylamine in 30 ml of 1,2-dichloroethane and the mixture is refluxed for 2 hours. The reaction mixture is concentrated under vacuum, the residue extracted with ether, washed with water, dried over $MgSO_4$ and the solvent evaporated under vacuum. The residue is chromatographed on silica H, eluting with the DCM/MeOH mixture (100/2; v/v). 2.5 g of the expected product are obtained.

B) 4-[(N',N'-Diethyl-N-methylureido)methyl]-4-phenylpiperidine p-toluenesulfonate.

A mixture of 2.4 g of the compound obtained in the preceding stage, 1 g of p-toluenesulfonic acid monohydrate, 0.24 g of 10% palladium on charcoal and 50 ml of MeOH is hydrogenated at 30° C. and at atmospheric pressure. The catalyst is filtered and the filtrate is evaporated under vacuum. 2.8 g of the expected product are obtained.

Preparation 1.7

4-Phenyl-4-(piperid-1-yl)piperidine dihydrochloride, dehydrate

A) 1-Benzyl-4-cyano-4-(piperid-1-yl)piperidine.

12.16 g of piperidine hydrochloride and 18.9 g of 1-benzylpiperid-4-one are dissolved in 50 ml of an MeOH/$H_2O$ mixture (50/50; v/v). 5.3 g of NaCN dissolved in 20 ml of water are added dropwise. After stirring for 48 hours, the precipitate formed is filtered, rinsed with water and dried to give 27 g of the expected product.

B) 1-Benzyl-4-phenyl-4-(piperid-1-yl)piperidine.

A solution of phenylmagnesium bromide is prepared from 1.5 g of magnesium, 12 g of phenyl bromide in 50 ml of ether. After stirring for 1 hour, a solution of 10 g of the compound obtained in the preceding stage in 100 ml of ether is added dropwise at RT and the mixture is kept stirring for 30 minutes. The reaction mixture is poured over 300 ml of a saturated solution of ammonium chloride, washed with water after decanting, extracted with a 2N solution of HCl, the acidic aqueous phase washed with DCM, the aqueous phase alkalinized by addition of concentrated NaOH, extracted with DCM, dried over $MgSO_4$ and the solvent evaporated under vacuum. The oil obtained is chromatographed on silica, eluting with the DCM/MeOH/$NH_4OH$ mixture (50/50/1; v/v/v). 4.2 g of the expected product are obtained after crystallization from isoether.

C) 4-Phenyl-4-(piperid-1-yl)piperidine dihydrochloride, dehydrate.

A solution of 1.6 g of CNBr in 20 ml of chloroform is added dropwise to a solution of 4 g of the compound obtained in the preceding stage in 25 ml of DCM and the mixture is refluxed for 1 hour. The reaction mixture is concentrated under vacuum, the residue taken up in 50 ml of a 6N solution of HCl and refluxed for 4 hours. Then the mixture is kept stirring overnight at RT, animal charcoal is added, and the mixture is filtered, the filtrate alkalinized by addition of 40% NaOH, extracted twice with ether, dried over $MgSO_4$ and evaporated under vacuum. The product obtained is taken up in DCM, acidified by addition of hydrochloric ether and evaporated under vacuum. 3 g of the expected product are obtained.

Preparation 1.8

4-(Formylamino)-4-phenylpiperidine hydrochloride
A) 1-Benzyl-4-(formylamino)-4-phenylpiperidine hydrochloride 4.5 ml of acetic anhydride are added dropwise to a solution of 2 g of the compound obtained in stage C of the PREPARATION 1.1, 0.9 g of sodium formate in 14 ml of formic acid and the mixture is kept stirring for 48 hours at RT. The reaction mixture is concentrated under vacuum, the residue taken up in water, alkalinized by addition of concentrated NaOH, extracted with DCM, dried over $MgSO_4$ and the solvent evaporated under vacuum. The product obtained is taken up in DCM, acidified to pH=1 by addition of hydrochloric ether and evaporated under vacuum. 1.7 g of the expected product are obtained after crystallization from acetone, m.p.=225° C. (dec).

B) 4-(Formylamino)-4-phenylpiperidine hydrochloride.

A mixture of 1.7 g of the compound obtained in the preceding stage, 0.2 g of 10% palladium on charcoal and 50 ml of 95% EtOH is hydrogenated at RT and at atmospheric pressure. The catalyst is filtered and the filtrate is evaporated under vacuum. 1.1 g of the expected product are obtained after crystallization from acetone, m.p.=217° C.

Preparation 1.9

4-(Formyl-N-ethylamino)-4-phenylpiperidine p-toluenesulfonate
A) 1-Benzyl-4-(N-ethylamino)-4-phenylpiperidine.

A solution of 5 g of 4-acetamido-1-benzyl-4-phenylpiperidine in 50 ml of THF is added to a suspension of 1.5 g of lithium aluminum hydride in 20 ml of THF and the mixture is refluxed for 3 hours. After cooling, a solution of 1 ml of concentrated NaOH in 8 ml of water is added, the inorganic salts are filtered and the filtrate is evaporated under vacuum. The oil obtained is dissolved in 50 ml of THF, this solution is added to a suspension of 1.5 ml of lithium aluminum hydride in 20 ml of THF and the mixture is refluxed for 1 hour. The reaction mixture is hydrolyzed by addition of a solution of 0.5 ml of concentrated NaOH in 6 ml of water, the inorganic salts filtered and the filtrate evaporated under vacuum. 4.8 g of the expected product are obtained, which product is used as it is in the next stage.

B) 1-Benzyl-4-(formyl-N-ethylamino)-4-phenylpiperidine p-toluenesulfonate.

13 ml of acetic anhydride are added dropwise to a solution of 4.8 g of the compound obtained in the preceding stage in 40 ml of formic acid and the mixture is heated at 40° C. for 24 hours. 30 ml of formic acid are added followed by 25 ml of acetic anhydride and the heating is continued at 40° C. for 24 hours. 30 ml of formic acid are again added followed by 25 ml of acetic anhydride and the heating is continued at 40° C. for 24 hours. The reaction mixture is concentrated under vacuum, the residue is taken up in water, alkalinized by addition of concentrated NaOH, extracted with DCM, dried over $MgSO_4$ and the solvent evaporated under vacuum. The residue is chromatographed on silica, eluting with DCM and then with the DCM/MeOH mixture (97/3; v/v). The product obtained is dissolved in 50 ml of acetone, 2.8 g of p-toluenesulfonic acid monohydrate are added and left to crystallize. 6.3 g of the expected product are obtained, m.p.=199° C.

C) 4-(Formyl-N-ethylamino)-4-phenylpiperidine p-toluene sulfonate.

A mixture of 6.3 g of the compound obtained in the preceding stage, 0.7 g of 10% palladium on charcoal and 100 ml of 95% EtOH is hydrogenated at RT and at atmospheric pressure. The catalyst is filtered and the filtrate is evaporated under vacuum. 4.78 g of the expected product are obtained after crystallization from the acetone/ether mixture, m.p.=151° C.

Preparation 1.10

4-(Cyclopropylcarbonyl-N-methylamino)-4-phenylpiperidine p-toluenesulfonate
A) 1-Benzyl-4-(N-methylamino)-4-phenylpiperidine.

A solution of 38.8 g of the compound obtained in stage A of the PREPARATION 1.8 (in the form of a free base, m.p.=140° C.) in 400 ml of THF is added dropwise to a suspension of 12.5 g of lithium aluminum hydride in 100 ml of THF and the mixture is refluxed for 3 hours. The reaction mixture is hydrolyzed by addition of a solution of 5 ml of concentrated NaOH in 45 ml of water, the inorganic salts filtered and the filtrate concentrated under vacuum. 38 g of the expected product are obtained, which product is used as it is in the next stage.

B) 1-Benzyl-4-(cyclopropylcarbonyl-N-methylamino)-4-phenylpiperidine.

A solution of 1.5 g of the compound obtained in the preceding stage, 1.5 ml of triethylamine in 20 ml of DCM, is cooled to 0° C., and 0.58 ml of cyclopropanecarbonyl chloride is added dropwise and the mixture is kept stirring for 2 hours while the temperature is allowed to rise to RT. The reaction mixture is washed twice with water, with a 1N solution of NaOH, dried over $MgSO_4$ and the solvent evaporated under vacuum. 1.8 g of the expected product are obtained.

C) 4-(Cyclopropylcarbonyl-N-methylamino)-4-phenylpiperidine p-toluenesulfonate.

A mixture of 1.8 g of the compound obtained in the preceding stage, 0.85 g of para-toluenesulfonic acid monohydrate, 0.35 g of 10% palladium on charcoal and 100 ml of EtOH is hydrogenated at RT and at atmospheric pressure. The catalyst is filtered on Celite® and the filtrate is evaporated under vacuum. 1.5 g of the expected product are obtained after crystallization from the acetone/AcOEt mixture.

Preparation 1.11

4-(Cyclopropylcarbonylamino)-4-phenylpiperidine hydrochloride
A) 1-Benzyl-4-(cyclopropylcarbonylamino)-4-phenylpiperidine.

A solution of 1 g of the compound obtained in stage C of the PREPARATION 1.1, 1.7 ml of triethylamine in 30 ml of DCM is cooled to −20° C., 0.22 ml of cyclopropanecarbonyl chloride is added dropwise and the mixture is kept stirring while allowing the temperature to rise to RT. The reaction mixture is extracted with DCM, washed twice with water, with a 0.5N solution of NaOH, dried over $MgSO_4$ and the solvent evaporated under vacuum. The residue is taken up in AcOEt, the crystals formed spun, washed with AcOEt and then with ether. 0.77 g of the expected product is obtained.

B) 4-(Cyclopropylcarbonylamino)-4-phenylpiperidine hydrochloride.

A mixture of 0.77 g of the compound obtained in the preceding stage, 0.14 g of 10% palladium on charcoal and 40 ml of EtOH is hydrogenated at 35° C. and at atmospheric pressure. The catalyst is filtered and the filtrate evaporated under vacuum. The residue is taken up in DCM, acidified to pH=1 by addition of hydrochloric ether and evaporated under vacuum. 0.6 g of the expected product is obtained.

Preparation 1.12

4-(Cyclobutylcarbonylamino)-4-phenylpiperidine hydrochloride

A) 1-Benzyl-4-(cyclobutylcarbonylamino)-4-phenylpiperidine.

A solution of 1.5 g of the compound obtained in stage C of the PREPARATION 1.1, 2.1 ml of triethylamine in 30 ml of DCM is cooled to 0° C., 0.45 ml of cyclobutanecarbonyl chloride is added dropwise and the mixture is kept stirring while allowing the temperature to rise to RT. The reaction mixture is extracted with DCM, washed twice with water, with a 0.5N solution of NaOH, dried over $MgSO_4$ and the solvent evaporated under vacuum. 1.1 g of the expected product are obtained after crystallization from AcOEt and then recrystallization from ether.

B) 4-(Cyclobutylcarbonylamino)-4-phenylpiperidine hydrochloride.

A mixture of 1.1 g of the compound obtained in the preceding stage, 0.18 g of 10% palladium on charcoal and 60 ml of EtOH is hydrogenated at 35° C. and at atmospheric pressure. The catalyst is filtered on Celite® and the filtrate is evaporated under vacuum. The residue is taken up in DCM, acidified by addition of hydrochloric ether and evaporated under vacuum. 0.92 g of the expected product is obtained.

Preparation 1.13

4-(Cyclohexylcarbonylamino)-4-phenylpiperidine hydrochloride

A) 1-Benzyl-4-(cyclohexylcarbonylamino)-4-phenylpiperidine.

This compound is prepared according to the procedure described in stage A of the PREPARATION 1.12 from 1.5 g of the compound obtained in stage C of the PREPARATION 1.1 and 0.75 ml of cyclohexanecarbonyl chloride. 1.3 g of the expected product are obtained.

B) 4-(Cyclohexylcarbonylamino)-4-phenylpiperidine hydrochloride.

This compound is prepared according to the procedure described in stage B of the PREPARATION 1.12. 0.9 g of the expected product is obtained.

Preparation 1.14

4-Methoxycarbonyl-4-phenylpiperidine p-toluenesulfonate 1 g of para-toluenesulfonic acid monohydrate is added to a solution of 10 g of 4-carboxy-4-phenylpiperidine p-toluenesulfonate in 300 ml of MeOH and the mixture is refluxed for 3 days. The reaction mixture is concentrated under vacuum, the residue taken up in acetone and ether is added until precipitation occurs. After spinning the precipitate formed, 9.34 g of the expected product are obtained.

Preparation 1.15

4-(N-methylcarbamoyl)-4-phenylpiperidine

A) 1-tert-Butoxycarbonyl-4-carboxy-4-phenylpiperidine.

30 ml of water, 32.9 g of $K_2CO_3$ are added to a mixture of 30 g of 4-carboxy-4-phenylpiperidine p-toluenesulfonate in 300 ml of dioxane, then the mixture is heated to 60° C. and 18.21 g of di-tert-butyl dicarbonate are added slowly. The reaction mixture is then heated for 2 hours at 60° C. and then refluxed for 30 minutes. The reaction mixture is concentrated under vacuum, the residue taken up in DCM, washed with buffer pH=2, acidified to pH=4 by addition of 2N HCl, extracted with DCM, washed with buffer pH=2, with water, with a saturated solution of NaCl, dried over $MgSO_4$ and evaporated under vacuum. 23.7 g of the expected product are obtained.

B) 1-tert-Butoxycarbonyl-4-(N-methylcarbamoyl)-4-phenylpiperidine.

1.98 g of triethylamine are added to a solution of 1.5 g of the compound obtained in the preceding stage in 5 ml of DCM and 5 ml of DMF, followed by 0.49 g of methylamine hydrochloride. The mixture is cooled on an ice bath, 2.39 g of BOP are added and the mixture is kept stirring for 24 hours while allowing the temperature to rise to RT. The reaction mixture is concentrated under vacuum, the residue extracted with ether, washed with water, with a buffer solution pH=2, with water, with a 10% solution of NaOH, with water, with a saturated solution of NaCl, dried over $MgSO_4$ and evaporated under vacuum. 1.4 g of the expected product are obtained.

C) 4-(N-Methylcarbamoyl)-4-phenylpiperidine.

4 ml of concentrated HCl are added to a solution of 1.4 g of the compound obtained in the preceding stage in 30 ml of MeOH and the mixture is kept stirring for 1 hour at RT. The reaction mixture is concentrated under vacuum, the residue extracted with DCM, washed with water, twice with a 10% solution of NaOH, dried over $MgSO_4$ and the solvent evaporated under vacuum. 0.6 g of the expected product is obtained.

Preparation 1.16

4-(N-n-Butylcarbamoyl)-4-phenylpiperidine

A) 1-tert-Butoxycarbonyl-4-(N-n-butylcarbamoyl)-4-phenylpiperidine.

This compound is prepared according to the procedure described in stage B of the PREPARATION 1.15 from 1.0 g of the compound obtained in stage A of the PREPARATION 1.15 and 0.24 g of n-butylamine. 1.3 g of the expected product are obtained, which product is used as it is in the next stage.

B) 4-(N-n-Butylcarbamoyl)-4-phenylpiperidine

This compound is prepared according to the procedure described in stage C of the PREPARATION 1.15. 0.4 g of the expected product is obtained.

Preparation 1.17

4-(N,N-Diethylcarbamoyl)-4-phenylpiperidine trifluoroacetate

A) 1-tert-Butoxycarbonyl-4-(N,N-diethylcarbamoyl)-4-phenylpiperidine.

This compound is prepared according to the procedure described in stage B of the PREPARATION 1.15 from 1.5 g of the compound obtained in stage A of the PREPARATION 1.15 and 0.8 g of diethylamine hydrochloride. 1.7 g of the expected product are obtained.

B) 4-(N,N-Diethylcarbamoyl)-4-phenylpiperidine trifluoroacetate.

1.7 g of the compound obtained in the preceding stage are dissolved in 20 ml of trifluoroacetic acid and the mixture is stirred at RT for 30 minutes. The reaction mixture is concentrated under vacuum, the residue taken up in ether and evaporated under vacuum. 2.8 g of the expected product are obtained in the form of an oil.

Preparation 1.18

4-(Pyrrolidin-1-ylcarbonyl)-4-phenylpiperidine

A) 1-tert-Butoxycarbonyl-4-(pyrrolidin-1-ylcarbonyl)-4-phenylpiperidine.

This compound is prepared according to the procedure described in stage B of the PREPARATION 1.15 from 1 g of the compound obtained in stage A of the PREPARATION 1.15 and 0.23 g of pyrrolidine. 1.0 g of the expected product is obtained.

B) 4-(Pyrrolidin-1-ylcarbonyl)-4-phenylpiperidine.

3 ml of concentrated HCl are added to a solution of 1.0 g of the compound obtained in the preceding stage in 25 ml of MeOH and the mixture is stirred for 1 hour at 35–40° C. The reaction mixture is concentrated under vacuum, the residue taken up in MeOH and the solvent evaporated under vacuum. The residue is extracted with ether, washed twice with a 10% solution of NaOH, with water, with a saturated solution of NaCl, dried over $MgSO_4$ and the solvent evaporated under vacuum. 0.43 g of the expected product is obtained.

Preparation 1.19

4-(N-Methoxy-N-methylcarbamoyl)-4-phenylpiperidine

A) 1-tert-Butoxycarbonyl-4-(N-methoxy-N-methylcarbamoyl)-4-phenylpiperidine.

This compound is prepared according to the procedure described in stage B of the PREPARATION 1.15 from 1.5 g of the compound obtained in stage A of the PREPARATION 1.15 and 0.71 g of O-methyl-N-methylhydroxylamine hydrochloride. 1.71 g of the expected product are obtained.

B) 4-(N-Methoxy-N-methylcarbamoyl)-4-phenylpiperidine.

This compound is prepared according to the procedure described in stage C of the PREPARATION 1.15 from 1.7 g of the compound obtained in the preceding stage. 1.1 g of the expected product are obtained.

Preparation 1.20

4-(Methylsulfonamido)-4-phenylpiperidine hydrochloride

A) 1-Benzyl-4-(methylsulfonamido)-4-phenylpiperidine p-toluenesulfonate.

A mixture of 5 g of the compound obtained in stage C of the PREPARATION 1.1, 10 ml of triethylamine in 100 ml of DCM is cooled to 0° C., under a nitrogen atmosphere, 2.68 g of mesyl chloride are added dropwise and the mixture is kept stirring for 30 minutes. The reaction mixture is concentrated under vacuum, the residue extracted with AcOEt, washed three times with water, with a 10% solution of NaOH, with a saturated solution of NaCl, dried over $MgSO_4$ and the solvent evaporated under vacuum. The oil obtained is dissolved in 50 ml of acetone, 2.8 g of p-toluenesulfonic acid monohydrate are added and, after stirring, the mixture is evaporated under vacuum. 6.8 g of the expected product are obtained.

B) 4-(Methylsulfonamido)-4-phenylpiperidine hydrochloride.

A 40% solution of NaOH is added to a solution of 6.8 g of the compound obtained in the preceding stage in water; the mixture is extracted with DCM, the organic phase is dried over $MgSO_4$ and the solvent is evaporated under vacuum. 2.3 g of 1-chloroethyl chloroformate, 1 ml of 1,2,2,6,6-pentamethylpiperidine are added to the residue obtained (3.69 g) and the mixture is kept stirring overnight. The reaction mixture is evaporated under vacuum, the residue is dissolved in MeOH and the mixture is heated at 60° C. for 1 hour. The solvent is evaporated under vacuum, the residue is taken up in acetone and the crystals formed are spun. 3 g of the expected product are obtained.

Preparation 1.21

4-(Methanesulfonyl-N-methylamino)-4-phenylpiperidine p-toluenesulfonate

A) 1-Benzyl-4-(methanesulfonyl-N-methylamino)-4-phenylpiperidine p-toluenesulfonate.

1.6 ml of triethylamine are added to a solution of 2 g of the compound obtained in stage A of the PREPARATION 1.10 in 30 ml of DCM followed by 0.9 ml of mesyl chloride and then the mixture is kept stirring for 30 minutes at RT. The reaction mixture is washed twice with water, with a 5% solution of NaOH, dried over $MgSO_4$ and the solvent evaporated under vacuum. The residue is taken up in ether, an insoluble matter is filtered and the filtrate is evaporated under vacuum. The residue is dissolved in acetone, 1.4 g of p-toluene-sulfonic acid monohydrate are added followed by ether until crystallization occurs. After spinning, 2.3 g of the expected product are obtained, m.p.=175° C.

B) 4-(Methanesulfonyl-N-methylamino)-4-phenylpiperidine p-toluenesulfonate.

A mixture of 2.3 g of the compound obtained in the preceding stage, 0.25 g of 10% palladium on charcoal in 40 ml of EtOH is hydrogenated at RT and at atmospheric pressure. The catalyst is filtered and the filtrate is evaporated under vacuum. 1.7 g of the expected product are obtained in the form of a foam.

Preparation 1.22

4-(Cyclopropylmethylamino)-4-phenylpiperidine di-p-toluenesulfonate

A) 4-(Cyclopropylcarbonylamino)-4-phenyl-1-tritylpiperidine.

A mixture of 0.565 g of 4-(cyclopropylcarbonylamino)-4-phenylpiperidine hydrochloride in 50 ml of DCM is cooled to +5° C., 0.565 g of trityl chloride is added followed by 0.7 ml of triethylamine and the mixture is kept stirring while allowing the temperature to rise to RT. The reaction mixture is washed with water, the organic phase dried over $MgSO_4$ and the solvent evaporated under vacuum. 1 g of the expected product is obtained after crystallization from ether.

B) 4-(Cyclopropylmethylamino)-4-phenyl-1-tritylpiperidine.

0.9 g of the compound obtained in the preceding stage is added to a suspension of 0.5 g of lithium aluminum hydride in 50 ml of THF and the mixture is refluxed for 30 minutes. The reaction mixture is hydrolyzed by addition of 0.4 ml of a solution of concentrated NaOH in 3 ml of water, the inorganic salts are filtered and the filtrate is evaporated under vacuum. The product obtained is added to a suspension of 0.7 g of lithium aluminum hydride in 50 ml of THF and the mixture is refluxed for 1 hour. The reaction mixture is hydrolyzed by addition of 0.5 ml of a concentrated solution of NaOH in 4 ml of water, the inorganic salts filtered and the filtrate evaporated under vacuum. 0.5 g of the expected product is obtained after crystallization from the DCM/isoether mixture.

C) 4-(Cyclopropylmethylamino)-4-phenylpiperidine di-p-toluenesulfonate.

A mixture of 0.5 g of the compound obtained in the preceding stage, 7.5 ml of formic acid and 7.5 ml of water is heated at 50° C. for 1 hour. The reaction mixture is filtered, the filtrate alkalinized by addition of a 40% solution of NaOH, extracted with DCM, dried over $MgSO_4$ and the solvent evaporated under vacuum. The product obtained is dissolved in DCM, 0.9 g of p-toluenesulfonic acid monohydrate is added and the mixture is refluxed. After cooling, the crystals formed are spun. 0.35 g of the expected product is obtained after recrystallization from the acetone/ether mixture.

Preparation 1.23

4-Hydroxymethyl-4-phenylpiperidine

A suspension of 1.16 g of lithium aluminum hydride in 50 ml of THF is cooled to −20° C., 4 g of the compound obtained in the PREPARATION 1.14 are added and the mixture is kept stirring overnight while allowing the temperature to rise to RT. The reaction mixture is hydrolyzed by addition of 1.2 ml of water, followed by 2.5 ml of a 10% solution of NaOH and 2.5 ml of water. The mixture is diluted with ether, the inorganic salts are filtered and the filtrate is evaporated under vacuum. 1.8 g of the expected product are obtained.

Preparation 1.24

4-Spiro(3-phthalide)piperidine hydrochloride
A) 1-Benzyl-4-spiro(3-phthalide)piperidine.

A solution of 10 g of N-methylbenzamide in 100 ml of THF is cooled to −70° C. and 100 ml of a 1.6M solution of n-butyllithium in hexane are added under nitrogen. The mixture is kept stirring while allowing the temperature to rise to 0° C., then cooled to −70° C. and 7 g of 1-benzylpiperid-4-one are added dropwise. The mixture is kept stirring for 30 minutes, the reaction mixture is poured over 1 liter of ice cold water, extracted twice with 500 ml of ether, the organic phase dried over $MgSO_4$ and the solvent evaporated under vacuum. The residue is chromatographed on silica, eluting with the DCM/MeOH mixture (99/1; v/v). 2.7 g of the expected product are obtained.
B) 4-Spiro(3-phthalide)piperidine hydrochloride.

A solution of 1 g of the compound obtained in the preceding stage, in 20 ml of DCM, is cooled to 0° C., 0.51 g of 1-chloroethyl chloroformate is added under a nitrogen atmosphere and the mixture is kept stirring for 2 hours at RT. The reaction mixture is concentrated under vacuum, the residue taken up in 10 ml of MeOH and heated at 50° C. for 35 minutes. The mixture is concentrated under vacuum. 0.66 g of the expected product is obtained after crystallization from acetone, m.p.=280° C. (dec).

Preparation 1.25

4-Hydroxy-4-(pyrid-2-yl)piperidine dihydrochloride
A) 1-Benzyl-4-hydroxy-4-(pyrid-2-yl)piperidine hydrochloride.

25 g of 2-bromopyridine are dissolved in 100 ml of THF at −70° C., under nitrogen, and a 1.6M solution of n-butyllithium in hexane is added dropwise followed by a solution of 30 g of 1-benzyl-piperid-4-one in 25 ml of THF. The temperature is allowed to rise to RT, and, after one hour, the solvents are partially evaporated, the residue is poured over a saturated solution of $NH_4Cl$, extracted with ether, washed with water, dried over $MgSO_4$ and evaporated. An oil is obtained which is dissolved in 200 ml of DCM and gaseous HCl is bubbled so as to form the hydrochloride. The expected product (21 g) crystallizes from a methanol/ether mixture, m.p.=185° C.
B) 4-Hydroxy-4-(pyrid-2-yl)piperidine dihydrochloride.

17.7 g of the compound obtained in the preceding stage are dissolved in a minimum of water, 40% sodium hydroxide is added, the mixture is extracted with DCM, dried over $MgSO_4$ and evaporated. 15 g of the product of stage A are thereby obtained in the form of a free amine. The product is dissolved in 150 ml of methanol, 2.5 g of 10% Pd/C and 17 g of ammonium formate are added. After stirring for 2 hours at RT and then refluxing for 2 hours, the mixture is evaporated, the residue is taken up in chloroform, washed with a 5% solution of sodium hydroxide, a saturated solution of NaCl, dried over $MgSO_4$ and evaporated. The residue is dissolved in methanol and forms the dihydrochloride (10 g) by addition of a 4N solution of HCl in ether, m.p.=230° C.

Preparation 1.26

4-Hydroxy-4-(2-methoxyphenyl)piperidine
A) 1-Benzyl-4-hydroxy-4-(2-methoxyphenyl)piperidine.

A solution of 15 g of 2-bromoanisole in 50 ml of THF is cooled to −70° C., under nitrogen, a 1.6 M solution of n-butyllithium in THF is added dropwise and the mixture is kept stirring for 1 hour. The mixture is is cooled to −70° C. and a solution of 15.2 g of 1-benzylpiperid-4-one in 50 ml of THF is added dropwise. The mixture is kept stirring while allowing the temperature to rise to RT and after 1 hour, the reaction mixture is concentrated under vacuum. The residue is taken up in AcOEt, the organic phase washed with water, with a saturated solution of NaCl, dried over $MgSO_4$ and the solvent evaporated under vacuum. 14 g of the expected product are obtained after crystallization from the AcOEt/ether/heptane mixture.
B) 4-Hydroxy-4-(2-methoxyphenyl)piperidine.

A mixture of 5 g of the compound obtained in the preceding stage, 1 g of 5% palladium on charcoal, 5 g of ammonium formate in 100 ml of MeOH is kept stirring for 2 hours. The reaction mixture is filtered and the filtrate evaporated under vacuum. The residue is taken up in DCM, the organic phase washed with a 40% NaOH solution, dried over $MgSO_4$ and the solvent evaporated under vacuum. 2.2 g of the expected product are obtained, m.p.=200° C.

Preparation 1.27

4-(Ethylaminocarbonyloxymethyl)-4-phenylpiperidine hydrochloride
A) 1-tert-Butoxycarbonyl-4-(hydroxymethyl)-4-phenylpiperidine.

26.05 g of di-tert-butyldicarbonate are added to a solution of 22.8 g of the compound obtained in the PREPARATION 1.23 in 250 ml of 1,2-dimethoxyethane and the mixture is refluxed for 2 hours. The reaction mixture is concentrated under vacuum, the residue taken up in DCM, the organic phase washed with a buffer solution pH=2, with a saturated NaCl solution, dried over $MgSO_4$ and the solvent evaporated under vacuum. 17.86 g of the expected product are obtained after crystallization from ether, m.p.=134° C.

B) 1-tert-Butoxycarbonyl-4-(ethylaminocarbonyloxymethyl)-4-phenylpiperidine.

A mixture of 2.91 g of the compound obtained in the preceding stage, 2.4 g of ethyl isocyanate, 2 drops of triethylamine in 30 ml of toluene is kept stirring overnight at RT. Then the reaction mixture is heated at 100° C. for 24 hours and concentrated under vacuum. The residue is taken up in ether, the organic phase washed with a buffer solution pH=2, with a saturated solution of NaCl, dried over MgSO$_4$ and the solvent evaporated under vacuum. 3.85 g of the expected product are obtained in the form of an oil.

C) 4-(Ethylaminocarbonyloxymethyl)-4-phenylpiperidine hydrochloride.

10 ml of concentrated HCl are added to a solution of 3.85 g of the compound obtained in the preceding stage in 50 ml of MeOH and the mixture is heated at 60° C. for 2 hours. The mixture is concentrated under vacuum, the residue taken up in acetone and the solvent evaporated under vacuum. 2.6 g of the expected product are obtained after crystallization from the AcOEt/ether mixture, m.p.=240–242° C.

Preparation 1.28

4-Phenyl-4-(propionyl-N-methylamino)piperidine p-toluenesulfonate

A) 4-(Acryloyl-N-methylamino)-1-benzyl-4-phenylpiperidine.

A solution of 1.5 g of the compound obtained in stage A of the PREPARATION 1.10, 1.5 ml of triethylamine in 40 ml of DCM is cooled to 0° C., 0.5 ml of acryloyl chloride is added dropwise and the mixture is kept stirring while allowing the temperature to rise to RT. The reaction mixture is poured into water, extracted with DCM, the organic phase washed with water, with a 2N solution of NaOH, dried over MgSO$_4$ and the solvent evaporated under vacuum. 1.3 g of the expected product are obtained after crystallization from the ether/pentane mixture.

B) 4-(Acryloyl-N-methylamino)-1-benzyl-4-phenylpiperidine p-toluenesulfonate.

0.59 g of p-toluenesulfonic acid monohydrate is added to a solution of 1.15 g of the compound obtained in the preceding stage in 10 ml of DCM and the mixture is allowed to crystallize. 1.65 g of the expected product are obtained.

C) 4-Phenyl-4-(propionyl-N-methylamino)piperidine p-toluenesulfonate.

A mixture of 1.64 g of the compound obtained in the preceding stage, 0.2 g of 10% palladium on charcoal in 100 ml of EtOH is hydrogenated at RT and at atmospheric pressure. The catalyst is filtered on Celite® and the solvent evaporated under vacuum. 1.3 g of the expected product are obtained.

Preparation 1.29

4-(Cyclohexylcarbonyl-N-methylamino)-4-phenylpiperidine p-toluenesulfonate

A) 1-Benzyl-4-(cyclohexylcarbonyl-N-methylamino)-4-phenylpiperidine p-toluenesulfonate.

0.78 ml of cyclohexanecarbonyl chloride is added at RT and dropwise to a solution of 1.5 g of the compound obtained in stage A of the PREPARATION 1.10, 1.5 ml of triethylamine in 15 ml of DCM and the mixture is kept stirring for 2 hours. The reaction mixture is washed twice with water, with a 2N solution of NaOH, the organic phase dried over MgSO$_4$ and the solvent evaporated under vacuum. The residue is dissolved in DCM, 0.97 g of p-toluenesulfonic acid monohydrate is added and the mixture is concentrated under vacuum. 3.3 g of the expected product are obtained after crystallization from the AcOEt/ether mixture.

B) 4-(Cyclohexylcarbonyl-N-methylamino)-4-phenylpiperidine p-toluenesulfonate.

A mixture of 3.3 g of the compound obtained in the preceding stage, 0.35 g of 10% palladium on charcoal in 100 ml of EtOH is hydrogenated at RT and at atmospheric pressure. The catalyst is filtered and the filtrate evaporated under vacuum. The residue is taken up in acetone and the solvent evaporated under vacuum. 2.2 g of the expected product are obtained after crystallization from the AcOEt/ether mixture, m.p.=160° C.

Preparation 1.30

4-Carbamoyl-4-phenylpiperidine

A) 1-tert-Butoxycarbonyl-4-carbamoyl-4-phenylpiperidine.

A solution of 1.5 g of the compound obtained in stage A of the PREPARATION 1.15, 0.99 g of triethylamine, 2.39 g of BOP in 10 ml of DCM is cooled to −20° C. and then ammonia gas is bubbled through the solution. The temperature is allowed to rise to RT and the mixture is kept stirring for 2 hours. The reaction mixture is concentrated under vacuum, the residue extracted with ether, the organic phase washed with water, with a buffer solution pH=2, with water, with a 10% solution of NaOH, with water, with a saturated solution of NaCl, dried over MgSO$_4$ and the solvent evaporated under vacuum. 1.32 g of the expected product are obtained.

B) 4-Carbamoyl-4-phenylpiperidine.

This compound is prepared according to the procedure described in stage C of the PREPARATION 1.15 from 1.32 g of the compound obtained in the preceding stage. 0.41 g of the expected product is obtained.

Preparation 1.31

4-(N,N-Dimethylcarbamoyl)-4-phenylpiperidine

A) 1-tert-Butoxycarbonyl-4-(N,N-dimethylcarbamoyl)-4-phenylpiperidine.

This compound is prepared according to the procedure described in stage B of the PREPARATION 1.15 from 1.5 g of the compound obtained in stage A of the PREPARATION 1.15 and 0.6 g of dimethylamine hydrochloride. 1.6 g of the expected product are obtained.

B) 4-(N,N-Dimethylcarbamoyl)-4-phenylpiperidine.

This compound is prepared according to the procedure described in stage C of the PREPARATION 1.15 from 1.6 g of the compound obtained in the preceding stage. 1.1 g of the expected product are obtained.

Preparation 1.32

4-(N-Isopropylcarbamoyl)-4-phenylpiperidine

A) 1-tert-Butoxycarbonyl-4-(N-isopropylcarbamoyl)-4-phenylpiperidine.

This compound is prepared according to the procedure described in stage B of the PREPARATION 1.15 from 1.5 g of the compound obtained in stage A of the PREPARATION 1.15 and 0.29 g of isopropylamine. 1.61 g of the expected product are obtained.

B) 4-(N-Isopropylcarbamoyl)-4-phenylpiperidine.

This compound is prepared according to the procedure described in stage C of the PREPARATION 1.15 from 1.61 g of the compound obtained in the preceding stage. 1.1 g of the expected product are obtained.

Preparation 2.1

2-(3,4-Dichlorophenyl)-5-(tetrahydropyran-2-yloxy)pentylamine

A) 2-(3,4-Dichlorphenyl)-5-(tetrahydropyran-2-yloxy)pentanenitrile.

15 g of sodium hydride at 60% in oil are suspended in 200 ml of anhydrous THF. A solution of 69.5 g of 3,4-dichlorophenylacetonitrile in 500 ml of THF is added dropwise over 30 minutes and then the reaction mixture is stirred at RT for 1 hour. The mixture is cooled to −20° C. and a solution of 85 g of 1-bromo-3-(tetrahydropyran-2-yloxy) propane in 100 ml of THF is added. The mixture is allowed to return to RT and after 2 hours it is poured over a solution of 50 g of ammonium chloride in 3 liters of water. The mixture is extracted with ether, washed with a saturated solution of sodium chloride, decanted, dried over $MgSO_4$ and concentrated. The residue is chromatographed on silica gel, eluting with a mixture of toluene and an AcOEt gradient (3 to 5%). The pure product fractions are concentrated to give 77 g of expected product in the form of an oil.

B) 2-(3,4-Dichlorophenyl)-5-(tetrahydropyran-2-yloxy) pentylamine.

77 g of nitrile obtained in the preceding stage are dissolved in 500 ml of absolute ethanol. 200 ml of concentrated ammonia are added followed by Raney® nickel (10% of the quantity of starting nitrile). The mixture is then hydrogenated under a hydrogen atmosphere at RT and atmospheric pressure, 10.5 l of hydrogen are absorbed and the catalyst separated by filtration on Celite®. The filtrate is concentrated under vacuum and the residue is taken up in a solution of NaCl. After extraction with ether and drying using $MgSO_{4.75}$ g of the expected product are obtained in the form of an oil.

Preparation 2.2

N-Methyl-2-(3,4-dichlorophenyl)-5-hydroxypentylamine hydrochloride

A) Ethyl N-[2-(3,4-dichlorophenyl)-5-(tetrahydropyran-2-yloxy)pentyl]carbamate.

20 g of the compound obtained in the PREPARATION 2.1 are dissolved in 200 ml of DCM and 9.3 ml of TEA are added. The mixture is cooled to −50° C. and a solution of 6.3 ml of ethyl chloroformate is added dropwise. After 15 minutes, the mixture is washed with water and then with dilute HCl. The mixture is dried over $MgSO_4$ and concentrated to dryness to give 24 g of oil.

B) N-Methyl-2-(3,4-dichlorophenyl)-5-(tetrahydropyran-2-yloxy)pentylamine.

A solution of 24 g of carbamate obtained in the preceding stage in 100 ml of anhydrous THF is added to 5 g of $LiAlH_4$ suspended in 150 ml of THF. The mixture is refluxed for 2 hours. The reaction mixture is hydrolyzed with 20 ml of water and 5 ml of concentrated sodium hydroxide, the inorganic material is filtered and to filtrate is concentrated to dryness. 20.1 g of the expected product are obtained in the form of an oil.

C) N-Methyl-2-(3,4-dichlorophenyl)-5-hydroxypentylamine hydrochloride.

20 g of the compound obtained in the preceding stage are dissolved in 200 ml of absolute ethanol. 8 ml of concentrated HCl are added and the mixture is stirred at RT for 2.5 hours. The reaction mixture is concentrated to dryness, ethanol and toluene are added and the mixture again concentrated to dryness. The residue is gradually crystallized from acetone by adding ether. It is filtered and dried. 15.8 g of the expected product are obtained, m.p.=124° C.

Preparation 2.3

3-(3,4-Dichlorophenyl)-3-(3-hydroxypropyl) piperidine hydrochloride

A) Methyl 4-cyano-4-(3,4-dichlorophenyl)heptanedioate.

37.2 g of 3,4-dichlorophenylacetonitrile and 34.43 g of methyl acrylate are dissolved in 20 ml of dioxane in a three-necked round-bottomed flask; 1 ml of DBU is added, the mixture is heated for 2 hours at 60° C., evaporated, diluted with 400 ml of ethyl acetate and then washed with dilute HCl, a solution of NaCl, dried over $MgSO_4$ and evaporated. The expected product is crystallized from 100 ml of ethyl acetate, and 100 ml of ether with 100 ml of heptane. 47 g of the product are obtained.

B) Methyl 3-[5-(3,4-dichlorophenyl)-2-oxopiperid-5-yl] propionate.

40 g of the compound prepared in stage A are dissolved in 500 ml of 2-methoxyethanol, 2 g of Raney® nickel are added and the mixture is hydrogenated at 40° C. at atmospheric pressure for 3 days. The mixture is filtered, evaporated and the expected product is obtained in the form of an oil (39 g).

C) 3-[5-(3,4-Dichlorophenyl)-2-oxopiperid-5-yl]propanoic acid.

17 g of the compound prepared in the preceding stage are dissolved in 250 ml of methanol, 2.8 g of potassium hydroxide and 10 ml of water are added and the mixture is refluxed for 2 hours. The reaction mixture is evaporated to dryness, the oil obtained taken up in 200 ml of water and extracted with 100 ml of ethyl acetate. The aqueous phase is acidified with a 30% solution of HCl and then the precipitate formed is filtered and dried. It is recrystallized from hot methanol and 18.3 g of the expected compound are obtained.

D) 3-(3,4-Dichlorophenyl)-3-(3-hydroxypropyl)piperidine hydrochloride.

5 g of the compound obtained in the preceding stage are dissolved in 20 ml of THF, 75 ml of borane (concentration 1M in THF) are added and the mixture is refluxed for 24 hours, under nitrogen. 25 ml of methanol, 50 ml of 4N HCl are added and the mixture is kept stirring for 30 minutes and then 40% sodium hydroxide is added up to a pH greater than 10. The reaction mixture is extracted 3 times with 150 ml of DCM, the organic phase dried over $MgSO_4$ and evaporated. The residue is dissolved in DCM with a 4N solution of HCl in ether. After evaporation, a foam is obtained and the expected product (4.5 g) crystallizes from the AcOEt/ether mixture.

EXAMPLE 1

N-Methyl-N-[2-(3,4-dichlorophenyl)-5-(4-hydroxy-4-phenylpiperid-1-yl)pentyl]benzamide hydrochloride A) N-[2-(3,4-Dichlorophenyl)-5-(tetrahydropyran-2-yloxy) pentyl]benzamide.

15 g of amine obtained in the PREPARATION 2.1 are dissolved in 200 ml of DCM. The solution is cooled to 0° C., 7 ml of TEA are added followed by 5.3 ml of benzoyl chloride. The reaction mixture is then stirred at RT for 30 minutes and then concentrated to dryness. The residue is taken up in ether, washed with water and then with a buffer solution pH=2 as well as a solution of $Na_2CO_3$. After drying and concentration, 19.5 g of the expected product are obtained in the form of an oil.

B) N-Methyl-N-[2-(3,4-dichlorophenyl)-5-tetrahydropyran-2-yloxypentyl]benzamide.

A mixture of 19.5 g of the compound prepared in the preceding stage and 3.1 g of sodium hydride at 60% in oil, in 200 ml of anhydrous THF is stirred at RT. The mixture is heated at 40° C. for 1 hour and 7.7 ml of methyl iodide are added. After stirring for 1 hour at 40° C., the mixture is concentrated to dryness, the residue is taken up in water, extracted with ether, washed with a buffer solution pH=2 and then with an Na$_2$CO$_3$ solution. It is dried over MgSO$_4$ and evaporated. 21 g of the expected product are obtained in the form of an oil.

C) N-Methyl-N-[2-(3,4-dichlorophenyl)-5-hydroxypentyl]benzamide.

21 g of the compound obtained in the preceding stage are dissolved in 170 ml of methanol in the presence of 5 ml of Amberlyst® 15 resin and the mixture is refluxed for 2 hours. The mixture is filtered on Celite®, the filtrate is concentrated under vacuum and the residue chromatographed on silica gel, eluent: DCM then DCM/AcOEt up to pure AcOEt. 13.5 g of the expected product are obtained in the form of an oil.

D) N-Methyl-N-[2-(3,4-dichlorophenyl)-5-mesyloxypentyl]-benzamide.

13.5 g of alcohol obtained in the preceding stage and 5.7 ml of TEA in 150 ml of DCM are stirred at 0° C. 3.2 ml of mesyl chloride are then added dropwise. After 15 minutes, the mixture is concentrated to dryness, taken up in ether and washed twice with water. The mixture is dried over MgSO$_4$ and the solvent evaporated. 16.2 g of the expected product are obtained in the form of an oil.

E) N-methyl-N-[2-(3,4-dichlorophenyl)-5-(4-hydroxy-4-phenylpiperid-1-yl)pentyl]benzamide.

A mixture of 1 g of mesylate obtained in the preceding stage, 800 mg of 4-hydroxy-4-phenylpiperidine and 3 ml of DMF is heated at 70° C. for 3 hours. After cooling, the mixture is poured over water and extracted with AcOEt and then washed with a solution of NaCl. The mixture is dried over MgSO$_4$ and the solvent evaporated. The product is chromatographed on silica, eluent: DCM with a MeOH gradient (2 to 5%). 400 mg of the expected product are obtained.

The hydrochloride of this compound is described in Application EP 474 561 in Example 22, m.p.=148° C.

EXAMPLE 2

N-Methyl-N-[2-(3,4-dichlorophenyl)-5-(4-propionyloxy-4-phenylpiperid-1-yl)pentyl]benzamide hydrochloride 400 mg of the compound obtained in Example 1 and 0.19 ml of TEA in 10 ml of DCM are stirred at RT. 0.13 ml of propionyl chloride is added dropwise and the mixture is washed with water then with a bicarbonate solution. The mixture is dried over MgSO$_4$ and the solvent evaporated. The product is chromatographed on silica gel, eluent: DCM with an MeOH gradient (from 1% to 2%). The hydrochloride is formed after dissolution in DCM and addition of hydrochloric ether. The solvent is evaporated and the hydrochloride is concreted from ether. 320 mg of the expected product are obtained, m.p.=112° C.

EXAMPLE 3

N-Methyl-N-(2-(3,4-dichlorophenyl)-5-(4-acetamido-4-phenylpiperid-1-yl)pentyl]phenylacetamide hydrochloride A) N-Boc-N-methyl-2-(3,4-dichlorophenyl)-5-hydroxypentylamine.

15.8 g of amino alcohol obtained in the PREPARATION 2.2 are dissolved in 150 ml of dioxane. 15 ml of water are added followed by 10 ml of TEA and 12.7 g of Boc$_2$O. The mixture is heated at 60° C. for 1 hour. The reaction mixture is then concentrated to dryness, taken up in ether, washed with water and then with a dilute solution of HCl. The mixture is dried over MgSO$_4$ and the solvent evaporated. 19.2 g of the expected product are obtained in the form of an oil.

B) N-Boc-N-methyl-2-(3,4-dichlorophenyl)-5-mesyloxypentylamine.

19.2 g of alcohol prepared in the preceding stage and 9.8 ml of TEA are stirred in 200 ml of DCM at 0° C. 5.4 ml of mesyl chloride are then added dropwise. After 15 minutes, the mixture is concentrated to dryness, taken up in ether, washed with water then with Na$_2$CO$_3$. The mixture is dried over MgSO$_4$ and the solvent evaporated. 23.5 g of the expected product are obtained in the form of an oil.

C) N-Boc-N-methyl-5-(4-acetamido-4-phenylpiperid-1-yl)-2-(3,4-dichlorophenyl)pentylamine.

A mixture of 10 g of mesylate obtained in the preceding stage, 14 g of 4-acetamido-4-phenylpiperidine and 20 ml of DMF is heated at 70° C. for 2 hours. After cooling, the mixture is poured over ice and extracted with AcOEt, washing with a dilute solution of sodium hydroxide and a solution of NaCl. The mixture is dried over MgSO$_4$ and the solvent evaporated. The product is chromatographed on silica, eluting with DCM containing MeOH (gradient up to 10%). 11.6 g of the expected product are obtained.

D) N-Methyl-5-(4-acetamido-4-phenylpiperid-1-yl)-2-(3,4-dichlorophenyl)pentylamine dihydrochloride.

11 g of the compound prepared in the preceding stage are dissolved in 50 ml of methanol. 20 ml of concentrated HCl are added and the mixture is stirred for 1 hour. The mixture is concentrated to dryness, taken up in a minimum of methanol and poured over ether. The mixture is filtered and dried to give 11.5 g of the expected product, m.p.=170° C.

E) N-Methyl-N-[2-(3,4-dichlorophenyl)-5-(4-acetamido-4-phenylpiperid-1-yl)pentyl]phenylacetamido hydrochloride 280 mg of phenylacetic acid are added to 1 g of the dihydrochloride obtained in the preceding stage dissolved in 20 ml of DCM, followed by 0.92 ml of TEA and 1 g of BOP. After stirring for 15 minutes at RT, the mixture is concentrated under vacuum, the residue taken up in AcOEt and washed successively with water, with a dilute solution of sodium hydroxide, with a solution of NaCl. The organic phase is dried over MgSO$_4$, filtered and concentrated under vacuum. The residue is chromatographed on silica gel, eluent: DCM with an MeOH gradient (3% to 6%). The hydrochloride is formed after dissolution in DCM and addition of hydrochloric ether. The solvent is evaporated and the hydrochloride is concreted from ether. 480 mg of the expected product are obtained, m.p.=137° C.

Other compounds according to the invention belonging to the family (II) have also been prepared and are described in TABLE 1 below.

TABLE 1

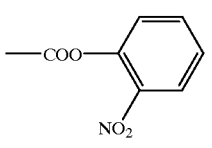

(II)

| Example N°. N° SR | R₂ | —T—A—Z— | m.p. ° C. |
|---|---|---|---|
| 4 | —NHCOCH₃ | —CO(CH₂)₂C₆H₅ | 119 |
| 5 | —NHCOCH₃ | —COOC₆H₅ | 138 |
| 6 | —NHCOCH₃ | —COOCH₂C₆H₅ | 120 |
| 7 | —NHCOCH₃ | —COO—(2-NO₂-C₆H₄) | 139 |
| 8 | —NHCOCH₃ | —COCH₂—(2-OCH₃-C₆H₄) | 133 |
| 9 | —NHCOCH₃ | —COCH=CH—C₆H₅ | 152 |
| 10 | —NHCOCH₃ | —CO(CH₂)₃C₆H₅ | 113 |
| 11 | —NHCOCH₃ | —COOCH₂—(4-Cl-C₆H₄) | 129 |
| 12 | —NHCOCH₃ | —COCH₂—(2-Cl-C₆H₄) | 125 |
| 13 | —OH | —COOCH₂C₆H₅ | 76 |
| 14 | —OCOC₂H₅ | —COOCH₂C₆H₅ | 86 |

EXAMPLE 15

1-Benzoyl-3-(3,4-dichlorophenyl)-3-[3-(4-pivaloylamino-4-phenylpiperid-1-yl)propyl] piperidine hydrochloride, (+)isomer A) 3-(3,4-Dichlorophenyl)-3-(3-hydroxypropyl)piperidine hydrochloride, (+)isomer.

10 g of the compound obtained in the PREPARATION 2.3 are dissolved in 20 ml of water, 5 ml of 40% sodium hydroxide are added, the mixture is extracted 3 times with 50 ml of DCM, the organic phase dried over MgSO₄ and evaporated to give 9 g of oil. 2.7 g of the oil obtained are dissolved in 50 ml of isopropanol, 2.36 g of 10-camphorsulfonic acid, (+)isomer, are added with the use of heat and the mixture is allowed to cool. The crystals formed (3.86 g) are dissolved in 10% NaOH, the mixture is extracted with chloroform, dried over MgSO₄ and evaporated. 2.3 g of the product are obtained in the form of an oil of which the hydrochloride is made. The specific rotation of the hydrochloride is measured.

$[\alpha]_D^{25}$=+5.5° (c=0.1; methanol).

A second crystallization carried out using 2.12 g of the oil obtained and 1.84 g of camphorsulfonic acid ((+)isomer) gives 3.27 g of crystals which, after basification with sodium hydroxide and extraction, give 2.10 g of the expected product in the form of an oil of which the hydrochloride is made.

$[\alpha]_D^{25}$=+6.5° (c=0.1; methanol).

After a third crystallization, the same specific rotation is obtained. The chiral purity, measured by chiral HPLC, is greater than 98%.

B) N-Boc-3-(3,4-dichlorophenyl)-3-(3-hydroxypropyl) piperidine, (+)isomer.

900 mg of the compound prepared in the preceding stage, 600 mg of TEA and 610 mg of (Boc)₂O are dissolved in 100 ml of DCM and the mixture is allowed to react under nitrogen, at RT for 30 minutes. The mixture is evaporated, the residue dissolved in AcOEt, washed with a buffer at pH=2, with dilute sodium hydroxide, a solution of NaCl and then dried over MgSO$_4$ and evaporated to give the expected product in the form of an oil (1.1 g).

C) N-Boc-3-(3,4-dichlorophenyl)-3-(3-mesyloxypropyl) piperidine, (+)isomer.

1.1 g of the compound obtained in the preceding stage are dissolved at 0° C. under nitrogen in 10 ml of DCM, 700 mg of TEA and 325 mg of mesyl chloride dissolved in 3 ml of DCM are added. After stirring for 2 hours, the mixture is evaporated, the residual oil taken up in AcOEt, washed with a buffer solution at pH 2, water, a solution of NaCl and then dried and evaporated. 1.4 g of the expected product are obtained in the form of an oil.

D) N-Boc-3-(3,4-dichlorophenyl)-3-[3-(4-pivaloylamino-4-phenylpiperid-1-yl)propyl]piperidine, (+)isomer.

1.4 g of the compound prepared in the preceding stage and 900 mg of 4-phenyl-4-pivaloylaminopiperidine obtained in the PREPARATION 1.1 are dissolved in 25 ml of acetonitrile. 450 mg of K$_2$CO$_3$ are added and the mixture is kept stirring for 2 hours at 60° C. The mixture is evaporated, dissolved in AcOEt, washed with a buffer solution at pH 2, a dilute solution of NaOH, a solution of NaCl, dried over MgSO$_4$ and evaporated to give 1.65 g of the expected product in the form of an oil.

E) 3-(3,4-Dichlorophenyl)-3-[3-(4-pivaloylamino-4-phenylpiperid-1-yl)propyl]piperidine hydrochloride, (+)isomer.

1.65 g of the compound prepared in the preceding stage and 5 ml of HCl at a concentration of 4N in ether are added to 25 ml of DCM. After stirring for 1 hour, 1.12 g of the expected compound are obtained.

F) 1-Benzoyl-3-(3,4-dichlorophenyl)-3-[3-(4-pivaloylamino-4-phenylpiperid-1-yl)propyl]piperidine hydrochloride, (+)isomer.

1.1 g of the compound obtained in the preceding stage, 800 mg of TEA and 252 mg of benzoyl chloride are dissolved in 15 ml of DCM, under nitrogen, at 0° C. After 15 minutes, the mixture is evaporated, dissolved in AcOEt, washed with a dilute solution of HCl, with a solution of NaCl, dried over MgSO$_4$ and evaporated. The foam obtained is chromatographed on silica, eluting with a DCM/MeOH mixture in a gradient up to 5%. The product obtained is salified by a solution of hydrochloric ether.

$[\alpha]_D^{25}$=+24.3 (c=0.1; methanol).

EXAMPLE 16

1-Benzoyl-3-(3,4-dichlorophenyl)-3-[3-(4-pivaloylamino-4-phenylpiperid-1-yl)propyl] piperidine hydrochloride, (−)isomer This compound is obtained as in EXAMPLE 15, using the camphorsulfonic acid, (−)isomer in stage A.

EXAMPLE 17

1-Benzoyl-3-(3,4-dichlorophenyl)-3-[3-(4-pivaloylamino-4-phenylpiperid-1-yl)propyl] piperidine hydrochloride, racemate This compound is obtained as in EXAMPLE 15 without carrying out the optical resolution of stage A.

EXAMPLE 18

1-Benzoyl-3-(3,4-dichlorophenyl)-3-[3-[4-(acetyl-N-methylamino)-4-phenylpiperid-1-yl)propyl] piperidine hydrochloride, monohydrate A) N-Boc-3-(3,4-dichlorophenyl)-3-(3-hydroxypropyl) piperidine.

A mixture of 23 g of the compound obtained in the PREPARATION 2.3, 15 g of triethylamine, 16 g of (Boc)$_2$O in 100 ml of DCM is kept stirring for 1 hour at RT and under a nitrogen atmosphere. The reaction mixture is concentrated under vacuum, the residue extracted with AcOEt, washed with a buffer solution pH=2, with a 5% solution of NaOH, with a saturated solution of NaCl, dried over MgSO$_4$ and the solvent evaporated under vacuum. 30 g of the expected product are obtained in the form of an oil.

B) N-Boc-3-(3,4-dichlorophenyl)-3-(3-mesyloxypropyl) piperidine.

A solution of 30 g of the compound obtained in the preceding stage, 15 ml of triethylamine in 200 ml of DCM is cooled to 0° C. and a solution of 9 g of mesyl chloride in 50 ml of DCM is added dropwise under a nitrogen atmosphere. The mixture is kept stirring for 2 hours and the solvent is evaporated under vacuum. The residue is extracted with AcOEt, washed with a buffer solution pH=2, with a 5% solution of NaOH, with a saturated solution of NaCl, dried over MgSO$_4$ and the solvent evaporated under vacuum. 34 g of the expected product are obtained.

C) N-Boc-3-(3,4-dichlorophenyl)-3-(3-[4-(acetyl-N-methylamino)-4-phenylpiperid-1-yl]propyl]piperidine.

A mixture of 1 g of the compound obtained in the preceding stage, 2 g of the compound obtained in the PREPARATION 1.3, 0.6 g of K$_2$CO$_3$ in 15 ml of DMF is heated at 60° C. for 3 hours, then the mixture is kept stirring overnight at RT. AcOEt is added to the reaction mixture, the organic phase is washed with water, with a saturated solution of NaCl, dried over MgSO$_4$ and the solvent evaporated under vacuum. The residue is chromatographed on silica H, eluting with the DCM/MeOH mixture (95/5; v/v). 0.78 g of the expected product is obtained.

D) 3-(3,4-Dichlorophenyl)-3-[3-[4-(acetyl-N-methylamino)-4-phenylpiperid-1-yl]propyl]piperidine hydrochloride.

2 ml of a saturated solution of HCl in ether are added to a solution of 0.78 g of the compound obtained in the preceding stage in 5 ml of DCM and the mixture is kept stirring for 1 hour at RT. The reaction mixture is evaporated under vacuum and 0.8 g of the expected product is obtained which is used as it is in the next stage.

E) 1-Benzoyl-3-(3,4-dichlorophenyl)-3-[3-[4-(acetyl-N-methylamino)-4-phenylpiperid-1-yl]propyl]piperidine hydrochloride, monohydrate.

A mixture of 0.75 g of the compound obtained in the preceding stage, 0.6 ml of triethylamine in 10 ml of DCM is cooled to 0° C. and 0.18 g of benzoyl chloride is added under a nitrogen atmosphere. The mixture is kept stirring for 2 hours at 0° C. and the reaction mixture is concentrated under vacuum. The residue is extracted with AcOEt, washed with a buffer solution pH=2, with a 5% solution of NaOH, with a saturated solution of NaCl, dried over MgSO$_4$ and the solvent evaporated under vacuum. The residue is chromatographed on silica H, eluting with the DCM/MeOH mixture (95/5; v/v). The product obtained is taken up in DCM, acidified to pH=1 by addition of hydrochloric ether and evaporated under vacuum. 0.5 g of the expected hydrochloride is obtained, m.p.=171° C.

EXAMPLE 19

1-Benzoyl-3-(3,4-dichlorophenyl)-3-[3-[4-(acetyl-N-methylamino)-4-phenylpiperid-1-yl]propyl] piperidine hydrochloride, monohydrate, (+)isomer A) 1-Benzoyl-3-(3,4-dichlorophenyl)-3-(3-hydroxypropyl)-piperidine, (+)isomer.

A solution of 7.45 g of the compound obtained in stage A of EXAMPLE 15 (in the form of a base) in 30 ml of DCM is cooled to −20° C. and 4 ml of triethylamine are added followed, dropwise, by 2.85 ml of benzoyl chloride. The mixture is kept stirring while allowing the temperature to rise to RT, then the reaction mixture is washed with a 0.5N solution of HCl, with a saturated solution of $Na_2CO_3$, the organic phase is dried over $MgSO_4$ and the solvent evaporated under vacuum. The residue is chromatographed on silica, eluting with the gradient of the DCM/AcOEt mixture from (90/10; v/v) to (80/20; v/v) then with DCM/MeOH (97/3; v/v). 9.40 g of the expected product are obtained.

B) 1-Benzoyl-3-(3, 4-dichlorophenyl)-3-(3-mesyloxypropyl)-piperidine, (+)isomer.

A solution of 9.4 g of the compound obtained in the preceding stage, 5 ml of triethylamine in 50 ml of DCM is cooled to −10° C. and 2.24 ml of mesyl chloride are added dropwise. The mixture is kept stirring while allowing the temperature to rise to RT and the solvent is concentrated under vacuum. The residue is extracted with AcOEt, washed twice with water, with a saturated solution of NaCl, dried over $MgSO_4$ and the solvent evaporated under vacuum. 10 g of the expected product are obtained.

C) 1-Benzoyl-3-(3,4-dichlorophenyl)-3-[3-[4-(acetyl-N-methylamino)-4-phenylpiperid-1-yl]propyl]piperidine hydrochloride, monohydrate, (+)isomer.

A mixture of 2 g of the compound obtained in the preceding stage, 4 g of 4-(acetyl-N-methylamino)-4-phenylpiperidine p-toluenesulfonate, 1 g of $K_2CO_3$ in 50 ml of acetonitrile and 50 ml of DMF is heated at 100° C. for 2 hours under a nitrogen atmosphere. The reaction mixture is concentrated under vacuum, the residue extracted with AcOEt, washed with water, with a 0.5N solution of HCl, with a 10% solution of NaOH, with a saturated solution of NaCl, dried over $MgSO_4$ and the solvent evaporated under vacuum. The residue is chromatographed on silica H, eluting with the gradient of the DCM/MeOH mixture from (99/1; v/v) to (95/5; v/v). The product obtained is taken up in DCM, acidified to pH=1 by addition of hydrochloric ether and evaporated under vacuum. 1.05 g of the expected product are obtained.

$[\alpha]_D^{25}$=+21.5°±0.5° (c=1; MeOH).

EXAMPLE 20

1-Benzoyl-3-(3,4-dichlorophenyl)-3-[3-[4-(acetyl-N-methylamino)-4-phenylpiperid-1-yl]propyl] piperidine hydrochloride, monohydrate, (−)isomer A) 3-(3,4-Dichlorophenyl)-3-(3-hydroxypropyl)piperidine hydrochloride, (−)isomer.

3.8 g of 10-camphorsulfonic acid, (−)isomer, are added to a solution of 4.7 g of the compound obtained in the PREPARATION 2.3, in the form of a free base, in 100 ml of isopropanol, and the mixture is refluxed. After cooling, crystallization and spinning of the crystals formed (4.90 g), the latter are dissolved in a 10% solution of NaOH, the mixture is extracted with chloroform, dried over $MgSO_4$ and the solvent evaporated under vacuum. 2.7 g of the product are obtained in the form of an oil of which the hydrochloride is made. The specific rotation of the hydrochloride is measured.

$[\alpha]_D^{25}$=−6.5° (c=1; MeOH).

A second crystallization is carried out from 2.6 g of the oil obtained, 2.77 g of 10-camphorsulfonic acid, (−)isomer, and 40 ml of isopropanol. After basification with sodium hydroxide, extraction with chloroform, drying over $MgSO_4$ and evaporation, the expected product is obtained in the form of an oil of which the hydrochloride is made. 2.4 g of the expected product are obtained.

$[\alpha]_D^{25}$=−6.8° (c=1; MeOH).

B) 1-Benzoyl-3-(3,4-dichlorophenyl)-3-(3-hydroxypropyl) piperidine, (−)isomer.

A solution of 11 g of the compound obtained in the preceding stage (in the form of a free base), 6 ml of triethylamine in 75 ml of DCM is cooled to −30° C. and 4.2 ml of benzoyl chloride are added dropwise. The mixture is kept stirring while allowing the temperature to rise to RT and then the reaction mixture is poured into water. The mixture is extracted with DCM, the organic phase washed with water, with a 0.5N solution of NaOH, dried over $MgSO_4$ and the solvent evaporated under vacuum. The residue is chromatographed on silica, eluting with the gradient of the DCM/AcOEt mixture from (85/15; v/v) to (75/25; v/v) and then with DCM/MeOH (97/3; v/v). 10 g of the expected product are obtained.

C) 1-Benzoyl-3-(3,4-dichlorophenyl)-3-(3-mesyloxypropyl) piperidine, (−)isomer.

A solution of 10 g of the compound obtained in the preceding stage, 5.5 ml of triethylamine in 100 ml of DCM is cooled to −30° C. and 2.4 ml of mesyl chloride are added dropwise. The mixture is kept stirring while allowing the temperature to rise to RT and concentrated under vacuum. The residue is extracted with AcOEt, washed twice with water, with a saturated solution of NaCl, dried over $MgSO_4$ and evaporated under vacuum. 11 g of the expected product are obtained.

D) 1-Benzoyl-3-(3,4-dichlorophenyl)-3-[3-[4-(acetyl-N-methylamino)-4-phenylpiperid-1-yl]propyl]piperidine hydrochloride, monohydrate, (−)isomer.

This compound is prepared according to the procedure described in stage C of EXAMPLE 19 from 0.5 g of the compound obtained in the preceding stage and 0.8 g of 4-(acetyl-N-methylamino)-4-phenylpiperidine p-toluene sulfonate. 0.375 g of the expected product is obtained.

$[\alpha]_D^{25}$=−21.5°±0.5 (c=1; MeOH).

According to a procedure similar to that described in Example 15, the compounds according to the invention which are described in Table 2 below are prepared:

TABLE 2

(III)

| Examples | Ar | R₂ | —T—A—Z | m.p. ° C. |
|---|---|---|---|---|
| 21 | —C₆H₅ | —NHCOCH₃ | —COC₆H₅ | 184 (1) |
| 22 | —C₆H₅ | —NHCOC₆H₅ | —COC₆H₅ | 140 |
| 23 | —C₆H₅ | —NH₂ | —COC₆H₅ | 210 |
| 24 | —C₆H₅ | —NHCOC₂H₅ | —COC₆H₅ | 187 |
| 25 | —C₆H₅ | —NHCOCH(CH₃)₂ | —COC₆H₅ | 170 |
| 26 | —C₆H₅ | —NHCOCH₃ | —COOCH₂C₆H₅ | 148 |
| 27 | —C₆H₅ | —NHCOCH₃ | —COCH₂C₆H₅ | 175 |
| 28 | —C₆H₅ | —NHCOCH₃ | —CH₂C₆H₅ | 200 |
| 29 | —C₆H₅ | —NHCO-(2-pyridyl) | —COC₆H₅ | 190 |
| 30 | —C₆H₅ | —NHCOCH₃ | —CO-(3-F-C₆H₄) | 191 |
| 31 | —C₆H₅ | —NHCOCH₃ | —CO-(2-F-C₆H₄) | 190 |
| 32 | (see structure below) | —OH | —COC₆H₅ | 169 |
| 33 | —C₆H₅ | —NHCOCH₃ | —CO-(4-F-C₆H₄) | 185 |
| 34 | —C₆H₅ | —NHCOCH₃ | —CONH-C₆H₅ | 212 |
| 35 | —C₆H₅ | —NCH₃COiPr | —COC₆H₅ | 192 |
| 36 | —C₆H₅ | —NHCOBu | —COC₆H₅ | 170 |
| 37 | —C₆H₅ | —OCH₃ | —COC₆H₅ | 180 |

Example 32 structure:

Phenyl-4-piperidine (with R₂)—N—(CH₂)₃—CH(3,4-dichlorophenyl)—CH₂—N(CH₃)—T—A—Z · HCl TABLE 2-continued (structure III: Ar-substituted piperidine-N-(CH₂)₃-[3-(3,4-dichlorophenyl)piperidine]-N-T-A-Z, HCl)

| Examples | Ar | R₂ | —T—A—Z | m.p. °C. |
|---|---|---|---|---|
| 38 | —C₆H₅ | —NHCOCH₃ | —CO-(3-chlorophenyl) | 250 |
| 39 | —C₆H₅ | —OH | —COC₆H₅ | 205 |
| 40 | —C₆H₅ | —OH | —CH₂-(3-methoxyphenyl) | 160 (1) (2) |
| 41 | —C₆H₅ | —NHCOCH₃ | —SO₂-phenyl | 195 |

(1) The preparation of these compounds is described in Application EP 512901, in Examples 27 and 29.
(2) Dihydrochloride (1) The preparation of these compounds is described in Application EP 512901, in Examples 27 and 29.
(2) Dihydrochloride

EXAMPLE 42

1-Benzoyl-3-(3,4-dichlorophenyl)-3-[3-(4-phenyl-(1,2,5,6-tetrahydropyrid-1-yl)propyl]piperidine hydrochloride This composition is prepared according to the procedure described above from 4-phenyl-(1,2,5,6-tetrahydropyridine) which is commercially available.

EXAMPLE 43

1-Benzoyl-3-(3,4-dichlorophenyl)-3-[3-(4-cyano-4-phenylpiperid-1-yl)propyl]piperidine hydrochloride A) 1-Benzoyl-3-(3,4-dichlorophenyl)-3-(3-hydroxypropyl) piperidine.

A solution of 16.22 g of the compound obtained in the PREPARATION 2.3, 18.2 g of triethylamine in 250 ml of DCM is cooled on an ice bath and a solution of 14.06 g of benzoyl chloride in 10 ml of DCM is added dropwise. The mixture is kept stirring for 1 hour while allowing the temperature to rise to RT. The excess benzoyl chloride is removed by addition of MeOH and the reaction mixture is then concentrated under vacuum. The residue is taken up in MeOH and the solvent evaporated under vacuum. The residue is extracted with ether, washed with water, with a 2N solution of HCl, with a 5% solution of NaHCO₃, with a saturated solution of NaCl, dried over MgSO₄ and evaporated under vacuum. The 1-benzoyl-3-(3,4-dichlorophenyl)-3-(3-benzoyloxypropyl)piperidine thus obtained as an intermediate is dissolved in 150 ml of MeOH, a solution of 10% NaOH is added, the mixture is heated for 1 hour at 50–60° C. and concentrated under vacuum. The residue is extracted with ether, washed with water, with a 2N solution of HCl, with a 5% solution of NaHCO₃, with a saturated solution of NaCl, dried over MgSO₄, and the solvent evaporated under vacuum. 18 g of the expected product are obtained in the form of an oil.

B) 1-Benzoyl-3-(3,4-dichlorophenyl)-3-(3-mesyloxypropyl) piperidine.

A solution of 16.8 g of the compound obtained in the preceding stage, 5.18 g of triethylamine in 100 ml of DCM is cooled on an ice bath and a solution of 5.40 g of mesyl chloride in 10 ml of DCM is added dropwise and then the mixture is kept stirring for 30 minutes while allowing the temperature to rise to RT. The reaction mixture is concentrated under vacuum, the residue is extracted with AcOEt, washed with water, with a 2N solution of HCl, with a saturated solution of NaCl, dried over MgSO₄ and the solvent evaporated under vacuum. 19.6 g of the expected product are obtained in the form of an oil.

NMR spectrum at 200 MHz in DMSO; 1 to 2.35 ppm: m: 8H; 3.15 ppm: s: 3H; 3.2 to 4.6 ppm: m: 6H; 6.8 to 7.8 ppm: m: 8H.

C) 1-Benzoyl-3-(3,4-dichlorophenyl)-3-[3-(4-cyano-4-phenylpiperid-1-yl)propyl piperidine hydrochloride.

A mixture of 5.9 g of the compound obtained in the preceding stage, 3 g of 4-cyano-4-phenylpiperidine, 6.9 g of K₂CO₃ in 20 ml of acetonitrile and 5 ml of DMF is refluxed for 2 hours. After cooling, the reaction mixture is poured into water, extracted with ether, washed with water, dried over MgSO$_4$ and the solvent evaporated under vacuum. The residue is chromatographed on silica H, eluting with the gradient of DCM/MeOH mixture from (100/1; v/v) to (100/2.5: v/v). The product obtained is taken up in DCM, acidified to pH=1 by addition of hydrochloric ether and evaporated under vacuum. 4.5 g of the expected hydrochloride are obtained after crystallization from the DCM/ether mixture, m.p.=239–241° C.

EXAMPLE 44

3-[3-[4-(Aminomethyl)-4-phenylpiperid-1-yl propyl]-1-benzoyl-3-(3,4-dichlorophenyl)piperidine dihydrochloride, dihydrate A mixture of 3.5 g of the compound obtained in EXAMPLE 43, 10 ml of a concentrated solution of NH$_{40}$H, 0.5 g of Raney® nickel, and 50 ml of EtOH is hydrogenated at RT and at atmospheric pressure. The catalyst is filtered and the filtrate evaporated under vacuum. The residue is extracted with DCM, washed with water, dried over MgSO$_4$ and the solvent evaporated under vacuum. The residue is taken up in DCM, acidified to pH=1 by addition of hydrochloric ether and evaporated under vacuum. 2.8 g of the expected product are obtained after crystallization from the DCM/ether mixture, m.p.=174° C.

EXAMPLE 45

1-Benzoyl-3-(3,4-dichlorophenyl)-3-[3-[4-[(N-ethoxycarbonylamino)methyl]-4-phenylpiperid-1-yl] propyl]piperidine hydrochloride, hemihydrate A solution of 1 g of the compound obtained in EXAMPLE 44, 0.535 g of triethylamine in 20 ml of DCM is cooled to 0° C. and 0.188 g of ethylchloroformate is added. The mixture is kept stirring for 30 minutes and concentrated under vacuum. The residue is extracted with ether, washed with water, dried over MgSO$_4$ and the solvent evaporated under vacuum. The residue is chromatographed on silica H, eluting with the gradient of the DCM/MeOH mixture from (100/3; v/v) to (100/5; v/v). The product obtained is taken up in DCM, acidified to pH=1 by addition of hydrochloric ether and evaporated under vacuum. 0.4 g of the expected product is obtained after crystallization from the DCM/ether mixture, m.p.=135–141° C. (dec).

EXAMPLE 46

1-Benzoyl-3-(3,4-dichlorophenyl)-3-[3-[4-[(N-propionylamino)methyl]-4-phenylpiperid-1-yl] propyl]piperidine hydrochloride, monohydrate 0.166 g of propionyl chloride is added to a solution of 0.87 g of the compound obtained in EXAMPLE 44, 0.3 g of triethylamine in 20 ml of DCM and the mixture is kept stirring for 30 minutes at RT. The mixture is concentrated under vacuum, the residue is extracted with AcOEt, washed with water, dried over MgSO$_4$ and evaporated under vacuum. The residue is chromatographed on silica H, eluting with the gradient of the DCM/MeOH mixture from (100/3; v/v) to (100/5; v/v). The residue is taken up in DCM, acidified to pH=1 by addition of hydrochloric ether and evaporated under vacuum. 0.49 g of the expected product is obtained after crystallization from the DCM/ether mixture, m.p.=143–149° C. (dec).

EXAMPLE 47

3-[3-[4-[(Acetyl-N-methylamino)methyl]-4-phenylpiperid-1-yl]propyl]-1-benzoyl-3-(3,4-dichlorophenyl)piperidine hydrochloride, monohydrate A mixture of 1.6 g of the compound obtained in stage B of EXAMPLE 43, 2 g of 4-[(acetyl-N-methylamino)-methyl]-4-phenylpiperidine p-toluenesulfonate, 2 g of K$_2$CO$_3$ and 4 ml of DMF is heated at 100° C. for 2 hours. After cooling, the reaction mixture is poured into water, extracted with ether, washed with water, dried over Na$_2$SO$_4$ and the solvent is evaporated under vacuum. The residue is chromatographed on silica H, eluting with the DCM/MeOH mixture (100/5; v/v). The product obtained is taken up in DCM, acidified to pH=1 by addition of hydrochloric ether and evaporated under vacuum. 0.75 g of the expected hydrochloride is obtained after crystallization from the DCM/ether mixture, m.p.=126° C.

EXAMPLE 48

1-Benzoyl-3-(3,4-dichlorophenyl)-3-[3-4-[(N'-ethyl-N-methylureido)methyl]-4-phenylpiperid-1-yl] propyl]piperidine hydrochloride, hemihydrate A mixture of 1.7 g of the compound obtained in stage B of EXAMPLE 43, 1.2 g of 4-[(N'-ethyl-N-methylureido) methyl]-4-phenylpiperidine, 1 g of K$_2$CO$_3$ and 5 ml of DMF is heated at 100° C. for 2 hours. After cooling, the reaction mixture is poured into water, extracted with the ether/AcOEt mixture, washed with water, dried over Na$_2$SO$_4$ and the solvent is evaporated under vacuum. The residue is chromatographed on silica H, eluting with the gradient of the DCM/MeOH mixture from (100/3; v/v) to (100/7; v/v). The product obtained is taken up in DCM, acidified to pH=1 by addition of hydrochloric ether and evaporated under vacuum. 1.15 g of the expected hydrochloride are obtained after crystallization from the DCM/ether mixture, m.p.=160° C.

EXAMPLE 49

1-Benzoyl-3-(3,4-dichlorophenyl)-3-[3-[4-[(N',N'-diethyl-N-methylureido)methyl]-4-phenylpiperid-1-yl]propyl]piperidine hydrochloride, hemihydrate This compound is prepared according to the procedure described in EXAMPLE 48 from 2 g of the compound obtained in stage B of EXAMPLE 43, 2.85 g of 4-[(N',N'-diethyl-N-methylureido)methyl]-4-phenylpiperidine p-toluenesulfonate, 2.5 g of K$_2$CO$_3$ and 4 ml of DMF. 0.9 g of the expected hydrochloride is obtained after crystallization from the DCM/ether mixture, m.p.=117–132° C. (dec).

EXAMPLE 50

1-Benzoyl-3-(3,4-dichlorophenyl)-3-[3-[4-(piperid-1-yl)-4-phenylpiperid-1-yl]propyl]piperidine dihydrochloride, dehydrate 1.7 g of 4-phenyl-4-(piperid-1-yl)piperidine dihydrochloride dehydrate are dissolved in a 40% solution of NaOH, the mixture is extracted with DCM, dried over MgSO$_4$ and the solvent evaporated under vacuum. The residue is taken up in 20 ml of DMF, 1.25 g of the compound obtained in stage B of EXAMPLE 43 are added and the mixture is heated at 100° C. for 2 hours. After cooling, the reaction mixture is diluted with DCM, the organic phase is washed with water, with a 1N solution of HCl, with a 5% solution of NaOH, with a saturated solution of NaCl, dried over MgSO$_4$ and the solvent evaporated under vacuum. The residue is chromatographed on silica H, eluting with the DCM/MeOH mixture (95/5; v/v). The product obtained is taken up in DCM, acidified to pH=1 by addition of hydrochloric ether and evaporated under vacuum. 1.2 g of the expected product are obtained, m.p.=192° C.

EXAMPLE 51

1-Benzoyl-3-(3,4-dichlorophenyl)-3-[3-[4-(formylamino)-4-phenylpiperid-1-yl]propyl]piperidine hydrochloride, monohydrate 0.55 g of 4-(formylamino)-4-phenylpiperidine hydrochloride is dissolved in water, the mixture is alkalinized by addition of concentrated NaOH, extracted with DCM, dried over $MgSO_4$ and the solvent evaporated under vacuum. The residue is taken up in 20 ml of acetonitrile, 0.9 g of the compound obtained in stage B of EXAMPLE 43 and 1 g of $K_2CO_3$ are added and the mixture is refluxed for 2 hours and 30 minutes. The mixture is concentrated under vacuum, the residue extracted with AcOEt, washed with water, with a 5% solution of NaOH, dried over $MgSO_4$ and the solvent evaporated under vacuum. The residue is chromatographed on silica H, eluting with DCM then with the DCM/MeOH mixture (90/10; v/v). The product obtained is taken up in DCM, acidified by addition of hydrochloric ether and evaporated under vacuum. 0.53 g of the expected product is obtained after crystallization from isoether.

NMR spectrum at 200 MHz in DMSO; 1.1 to 2.65 ppm: m: 12H; 2.7 to 4.5 ppm: m: 10H; 7.0 to 7.7 ppm: m: 13H; 8.0 ppm: s: 1H; 8.4 ppm: s: 1H; 10.5 ppm: bs: 1H.

EXAMPLE 52

1-Benzoyl-3-(3,4-dichlorophenyl)-3-[3-[4-(cyclopropylcarbonylamino)-4-phenylpiperid-1-yl]propyl]piperidine hydrochloride, monohydrate 0.370 g of 4-(cyclopropylcarbonylamino)-4-phenylpiperidine hydrochloride is dissolved in water, the mixture is alkalinized by addition of concentrated NaOH, extracted with DCM, dried over $MgSO_4$ and the solvent evaporated under vacuum. The residue is taken up in 10 ml of DMF, 0.655 g of the compound obtained in stage B of EXAMPLE 43 and 0.192 g of $K_2CO_3$ are added and the mixture is heated at 80° C. for 30 minutes. After stirring overnight at RT, the reaction mixture is poured into water, extracted with AcOEt, washed twice with water, with a saturated solution of NaCl, dried over $MgSO_4$ and the solvent evaporated under vacuum. The residue is chromatographed on silica, eluting with DCM, and then with the DCM/MeOH mixture (95/5; v/v). The product obtained is taken up in DCM, acidified to pH=1 by addition of hydrochloric ether and evaporated under vacuum. 0.27 g of the expected product is obtained.

NMR spectrum at 200 MHz in DMSO; 0.6 ppm: mt: 4H; 1.0 to 2.7 ppm: m: 13H; 2.75 to 4.5 ppm: m: 10H; 7.0 to 7.9 ppm: m: 13H; 8.4 ppm: s: 1H; 10 ppm: bs: 1H.

EXAMPLE 53

1-Benzoyl-3-(3,4-dichlorophenyl)-3-[3-[4-methoxycarbonyl-4-phenylpiperid-1-yl]propyl]piperidine hydrochloride, hemihydrate A mixture of 0.9 g of 4-methoxycarbonyl-4-phenylpiperidine p-toluenesulfonate, 0.91 g of the compound obtained in stage B of EXAMPLE 43, 1.06 g of $K_2CO_3$ in 5 ml of DMF and 5 ml of acetonitrile is refluxed for 3 hours. The reaction mixture is poured into water, extracted with AcOEt, washed twice with water, with a saturated solution of NaCl, dried over $MgSO_4$ and the solvent evaporated under vacuum. The residue is chromatographed on silica H, eluting with DCM, and then with the DCM/MeOH mixture (97/3; v/v). The product obtained is taken up in AcOEt, acidified by addition of hydrochloric ether and evaporated under vacuum. 0.54 g of the expected product is obtained after crystallization from the acetone/ether mixture, m.p.=123–125° C.

EXAMPLE 54

1-Benzoyl-3-(3,4-dichlorophenyl)-3-[3-[4-(N,N-diethylcarbamoyl)-4-phenylpiperid-1-yl]propyl]piperidine hydrochloride, monohydrate This compound is prepared according to the procedure described in EXAMPLE 53 from 1.7 g of 4-(N,N-diethylcarbamoyl)-4-phenylpiperidine trifluoroacetate, 1.77 g of the compound obtained in stage B of EXAMPLE 43, 2.08 g of $K_2CO_3$, 5 ml of DMF and 5 ml of acetonitrile. 1.1 g of the expected product are obtained, m.p.=124–126° C.

EXAMPLE 55

1-Benzoyl-3-(3,4-dichlorophenyl)-3-[3-(4-(N-methoxy-N-methylcarbamoyl)-4-phenylpiperid-1-yl]propyl]piperidine hydrochloride, hemihydrate This compound is prepared according to the procedure described in EXAMPLE 53 from 1.1 g of 4-(N-methoxy-N-methylcarbamoyl)-4-phenylpiperidine, 1.73 g of the compound obtained in stage B of EXAMPLE 43, 1.52 g of $K_2CO_3$, 5 ml of DMF and 5 ml of acetonitrile. 0.99 g of the expected product is obtained, m.p.=155–157° C.

EXAMPLE 56

1-Benzoyl-3-(3,4-dichlorophenyl)-3-[3-[4-(methylsulfonamido)-4-phenylpiperid-1-yl]propyl]piperidine hydrochloride, hemihydrate 1.6 g of 4-(methylsulfonamido)-4-phenylpiperidine hydrochloride are dissolved in a minimum of a 40% solution of sodium hydroxide, the mixture is extracted with DCM, the organic phase dried over $MgSO_4$ and the solvent evaporated under vacuum. The residue is dissolved in 25 ml of DMF, 1.29 g of the compound obtained in stage B of EXAMPLE 43 are added and the mixture is heated, under a nitrogen atmosphere, at 80° C. for 2 hours. The reaction mixture is poured into water, the precipitate formed spun and washed with water. The precipitate is dissolved in DCM, the organic phase is washed twice with water, dried over $MgSO_4$ and the solvent evaporated under vacuum. The residue is chromatographed on silica H, eluting with DCM, and then with the DCM/MeOH mixture (95/5; v/v). The product obtained is taken up in DCM, acidified by addition of hydrochloric ether and evaporated under vacuum. 0.7 g of the expected product is obtained, m.p.=210° C.

EXAMPLE 57

1-Benzoyl-3-(3,4-dichlorophenyl)-3-[3-[4-(methanesulfonyl-N-methylamino)-4-phenylpiperid-1-yl]propyl]piperidine hydrochloride, hemihydrate A mixture of 0.79 g of 4-(methanesulfonyl-N-methylamino)-4-phenylpiperidine p-toluenesulfonate, 0.70 g of the compound obtained in stage B of EXAMPLE 43, 0.80 g of $K_2CO_3$ and 10 ml of acetonitrile is refluxed for 3 hours. The reaction mixture is concentrated under vacuum, the residue taken up in water, extracted with AcOEt, washed with a 5% solution of NaOH, dried over $MgSO_4$ and the solvent evaporated under vacuum. The residue is chromatographed on silica H, eluting with DCM, and then with the DCM/MeOH mixture (95/5; v/v). The product obtained is taken up in DCM, acidified by addition of hydrochloric ether and evaporated under vacuum. 0.71 g of the expected product is obtained after crystallization from ether.

NMR spectrum at 200 MHz in DMSO; 1.0 to 2.45 ppm: m: 15H; 2.45 to 4.50 ppm: m: 13H; 7.0 to 7.9 ppm: m: 13H; 10.75 ppm: s: 1H.

EXAMPLE 58

1-Benzoyl-3-(3,4-dichlorophenyl)-3-[3-[4-(propionyloxy)-4-phenylpiperid-1-yl]propyl]piperidine hydrochloride, hemihydrate A solution of 0.95 g of the compound obtained in EXAMPLE 39, 0.4 ml of triethylamine in 50 ml of DCM is cooled to 0° C., 0.15 ml of propionyl chloride is added dropwise and the mixture is kept stirring while allowing the temperature to rise to RT. The reaction mixture is concentrated under vacuum and the residue is chromatographed on silica, eluting with the gradient of the DCM/MeOH mixture from (99/1; v/v) to (97/3; v/v). The product obtained is taken up in DCM, acidified by addition of hydrochloric ether and evaporated under vacuum. 0.5 g of the expected product is obtained.

NMR spectrum at 200 MHz in DMSO; 1.0 ppm: t: 3H; 1.15 to 2.0 ppm: m: 6H; 2.0 to 2.8 ppm: m: 8H; 2.9 to 4.6 ppm: m: 10H; 7.1 to 7.9 ppm: m: 13H; 10.2 ppm: bs: 1H.

EXAMPLE 59

1-Benzoyl-3-(3,4-dichlorophenyl)-3-[3-[4-(spiro(phthalide-3)piperid-1-yl]propyl]piperidine hydrochloride, monohydrate A mixture of 1.4 g of 4-spiro(3-phthalide)piperidine hydrochloride, 0.715 g of potassium tert-butoxide and 15 ml of DMF is stirred for 5 minutes. 2.5 g of the compound obtained in stage B of EXAMPLE 43, 2 g of $K_2CO_3$ are then added and the mixture is heated at 100° C. for 45 minutes and kept stirring overnight at RT. The reaction mixture is diluted by addition of AcOEt, the organic phase is washed with a buffer solution pH=2, with a 5% solution of NaOH, with a saturated solution of NaCl, dried over $MgSO_4$ and evaporated under vacuum. The residue is chromatographed on silica H, eluting with a gradient of the DCM/MeOH mixture from (99/1; v/v) to (95/5; v/v). The product obtained is taken up in DCM, acidified by addition of hydrochloric ether and evaporated under vacuum. 0.77 g of the expected product is obtained, m.p.=165° C.

The compounds according to the invention which are described in TABLE 3 below are prepared according to the procedures described in the EXAMPLES above.

TABLE 3

(III)

| Examples | Ar | $R_2$ | —T—A—Z | Solvate m.p. ° C. or NMR |
|---|---|---|---|---|
| 60 (a) | —$C_6H_5$ | —N(Et)—C(O)—H | —$COC_6H_5$ | 0.5 $H_2O$ NMR |
| 61 (a) | —$C_6H_5$ | —N(Me)—CO—cyclopropyl | —$COC_6H_5$ | 0.5 $H_2O$ NMR |
| 62 (b) | —$C_6H_5$ | —NH—CO—cyclobutyl | —$COC_6H_5$ | 1 $H_2O$ NMR |
| 63 (b) | —$C_6H_5$ | —NH—CO—cyclohexyl | —$COC_6H_5$ | 1 $H_2O$ NMR |
| 64 (c) | —$C_6H_5$ | —C(O)—Me | —$COC_6H_5$ | 0.5 $H_2O$ 130–135 |

TABLE 3-continued

Structure (III): Ar-R₂-substituted piperidine—N—(CH₂)₃—[piperidine with 3,4-dichlorophenyl]—N—T—A—Z, HCl

| Examples | Ar | R₂ | —T—A—Z | Solvate m.p. °C. or NMR |
|---|---|---|---|---|
| 65 (d) | —C₆H₅ | —C(=O)—NH—Me | —COC₆H₅ | 1 H₂O 155–157 |
| 66 (d) | —C₆H₅ | —C(=O)—NH-Bu | —COC₆H₅ | 1 H₂O 130–132 |
| 67 (d) | —C₆H₅ | —C(=O)—N(pyrrolidine) | —COC₆H₅ | 1 H₂O 144–146 |
| 68 (a) | —C₆H₅ | —NH—CH₂-cyclopropyl | —COC₆H₅ | 1 H₂O 190 |
| 69 (d) | —C₆H₅ | —CH₂—OH | —COC₆H₅ | 0.5 H₂O 146–148 |
| 70 (d) | —C₆H₅ | —CH₂—O—C(=O)—NH-Et | —COC₆H₅ | 0.5 H₂O 133–135 |
| 71 (d) | —C₆H₅ | —N(Me)—C(=O)-Et | —COC₆H₅ | 1 H₂O 135 |
| 72 (d) | —C₆H₅ | —N(Me)—CO-cyclohexyl | —COC₆H₅ | 0.5 H₂O 135 |
| 73 (d) | —C₆H₅ | —C(=O)—NH₂ | —COC₆H₅ | 0.5 H₂O 246–248 |
| 74 (d) | —C₆H₅ | —C(=O)—N(Me)(Me) | —COC₆H₅ | 1 H₂O 140–142 |
| 75 (d) | —C₆H₅ | —C(=O)—NH—iPr | —COC₆H₅ | 1 H₂O 140–142 |

(a) this compound is prepared according to the procedure described in EXAMPLE 47
(b) this compound is prepared according to the procedure described in EXAMPLE 52
(c) this compound is prepared according to the procedure described in EXAMPLE 43 Stage C
(d) this compound is prepared according to the procedure described in EXAMPLE 53.

(a) this compound is prepared according to the procedure described in EXAMPLE 47

(b) this compound is prepared according to the procedure described in EXAMPLE 52

(c) this compound is prepared according to the procedure described in EXAMPLE 43 stage C (d) this compound is prepared according to the procedure described in EXAMPLE 53.

NMR spectrum at 200 MHz in DMSO of the compound of EXAMPLE 60; 0.85 ppm: st: 3H; 1.0 to 2.5 ppm: m: 12H; 2.5 to 4.5 ppm; m: 12H; 7.0 to 7.9 ppm: m: 13H; 8.3 to 8.6 ppm: ss: 1H; 9.2 to 11.0 ppm: ss: 1H.

NMR spectrum at 200 MHz in DMSO of the compound of EXAMPLE 61; 0.7 to 2.3 ppm: m: 13H; 2.6 to 4.6 ppm: m: 15H; 7.0 to 7.9 ppm: m: 13H; 10.3 ppm: bs; 1H.

NMR spectrum at 200 MHz in DMSO of the compound of EXAMPLE 62; 1.4 to 3.1 ppm: m: 19H; 3.15 to 4.9 ppm: m: 10H; 7.1 to 7.8 ppm: m: 13H; 7.95 ppm: s: 1H; 10.0 ppm: bs: 1H.

NMR spectrum at 200 MHz in DMSO of the compound of EXAMPLE 63; 0.8 to 2.7 ppm: m: 23H; 2.75 to 4.6 ppm: m: 10H; 7.0 to 8.0 ppm: m: 13H; 8.0 ppm: s: 1H; 10.2 ppm: bs: 1H.

EXAMPLE 76

1-Benzoyl-3-(3,4-dichlorophenyl)-3-[3-[4-hydroxy-4-(2-methoxyphenyl)piperid-1-yl]propyl]piperidine hydrochloride, 1.5-hydrate A mixture of 1.80 g of 4-hydroxy-4-(2-methoxyphenyl) piperidine, 1.92 g of the compound obtained in stage B of EXAMPLE 43 in 10 ml of DMF is heated at 80° C. for 2 hours. The reaction mixture is poured into water, the precipitate formed spun and washed with water. The precipitate is dissolved in chloroform, the organic phase is washed with water, with a buffer solution pH=2 and dried over $MgSO_4$ and the solvent evaporated under vacuum. The residue is chromatographed on silica H, eluting with the gradient of the DCM/MeOH mixture from (99/1; v/v) to (97/3; v/v). The product obtained is taken up in hydrochloric ether and the precipitate formed is spun. 0.7 g of the expected product is obtained, m.p.=180° C.

EXAMPLE 77

1-(4-Iodobenzoyl)-3-(3,4-dichlorophenyl)-3-[3-[4-(acetyl-N-methylamino)-4-phenylpiperid-1-yl] propyl]piperidine hydrochloride, monohydrate, (+) isomer A) 1-(4-Iodobenzoyl)-3-(3,4-dichlorophenyl)-3-(3-hydroxypropyl)piperidine, (+)isomer.

6.5 ml of triethylamine are added at RT to a mixture of 5 g of the compound obtained in stage A of EXAMPLE 15, 3.9 g of 4-iodobenzoic acid in 100 ml of DCM, followed by 8.2 g of BOP and the mixture is kept stirring for 15 minutes at RT. The reaction mixture is concentrated under vacuum, the residue is taken up in ether, the organic phase is washed with water, with a 1N solution of NaOH, with water, with a 1N solution of HCl, with a saturated solution of NaCl, dried over $MgSO_4$ and the solvent evaporated under vacuum. The residue is chromatographed on silica, eluting with DCM and then with the DCM/AcOEt mixture (50/50; v/v) and then with AcOEt. 8.5 g of the expected product are obtained.

B) 1-(4-Iodobenzoyl)-3-(3,4-dichlorophenyl)-3-(3-mesyloxypropyl)piperidine, (+)isomer.

A solution of 8.5 g of the compound obtained in the preceding stage, 2.7 ml of triethylamine in 150 ml of DCM is cooled to 0° C. and 1.5 ml of mesyl chloride are added dropwise. The mixture is kept stirring while allowing the temperature to rise to RT and the mixture is concentrated under vacuum. The residue is extracted with ether, the organic phase is washed twice with water, dried over $MgSO_4$ and the solvent evaporated under vacuum. 10 g of the expected product are obtained.

C) 1-(4-Iodobenzoyl)-3-(3,4-dichlorophenyl)-3-[3-[4-acetyl-N-methylamino)-4-phenylpiperid-1-yl]propyl] piperidine hydrochloride, monohydrate, (+)isomer A mixture of 10 g of the compound obtained in the preceding stage, 8.2 g of 4-(acetyl-N-methylamino)-4-phenylpiperidine p-toluenesulfonate, 9.3 g of $K_2CO_3$ in 80 ml of DMF is heated at 80° C. for 1 hour. Then 4 g of 4-(acetyl-N-methylamino)-4-phenylpiperidine p-toluene sulfonate are added to the reaction mixture and the heating is continued at 80° C. for 2 hours. After cooling, the reaction mixture is poured into ice-cold water, the precipitate formed is spun and washed with water. The precipitate is dissolved in DCM, the organic phase is dried over $MgSO_4$ and the solvent evaporated under vacuum. The residue is chromatographed on silica H, eluting with DCM, then with the DCM/MeOH mixture (95/5; v/v). The product obtained is taken up in DCM, acidified to pH=1 by addition of hydrochloric ether and evaporated under vacuum. 9.2 g of the expected product are obtained after crystallization from ether, m.p.=172° C. (dec).

$[\alpha]_D^{25}=+27.2°$ (c==1; MeOH).

What is claimed is:

1. A compound which is selected from the group consisting of:

1-benzoyl-3-(3,4-dichlorophenyl)-3-[3-(4-(acetyl-N-methylamino)-4-phenylpiperid-1-yl)propyl]piperidine, 1-benzoyl-3-(3,4-chlorophenyl)-3-[3-(4-(propionyl-N-methylamino)-4-phenylpiperid-1-yl)propyl]piperidine, 1-benzoyl-3-(3,4-dichlorophenyl)-3-[-3-(4-(butyryl-N-methylamino)-4-phenylpiperid-1-yl)propyl]piperidine, 1-benzoyl-3-(3,4-dichlorophenyl)-3-[3-(4-(isobutyryl-N-methylamino)-4-phenyl-piperid-1-yl)propyl] piperidine, 1-benzoyl-3-(3,4chlorophenyl)-3-[3-(4-(valeryl-N-methylamino)-4-phenylpiperid-1-yl)propyl]piperidine, 1-benzoyl-3-(3,4-chlorophenyl)-3-[3-(4-(isovaleryl-N-methylamino)-4-phenylpiperid-1-yl)propyl]piperidine, 1-benzoyl-3-(3,4-dichlorophenyl)-3-[3-(4-(pivaloyl-N-methylamino)-4-phenylpiperid-1-yl)propyl]piperidine, and their salts, wherein said compound is in the form of a (+) enantiomer.

2. (+)-1-benzoyl-3-(3,4-dichlorophenyl)-3-[3-(4-(acetyl-N-methylamino)-4-phenylpiperid-1-yl)-propyl]piperidine, or one of its salt.

3. A compound according to claim 2, which is (+)-1-benzoyl-3-(3,4-dichlorophenyl)-3-[3-(4-(acetyl-N-methylamino)-4-phenylpiperid-1-yl)-propyl]piperidine hydrochloride.

4. A pharmaceutical composition comprising a therapeutically effective amount of a compound according to claim 1, or a pharmaceutically acceptable salt thereof, and a pharmaceutical carrier.

5. A pharmaceutical composition according to claim 4, comprising from 0.5 to 1000 mg of said compound.

6. A pharmaceutical composition according to claim 5, comprising from 2.5 to 250 mg of said compound.

7. A pharmaceutical composition comprising a therapeutically effective amount of a compound according to claim 2, or a pharmaceutically acceptable salt thereof, and a pharmaceutical carrier.

8. A pharmaceutical composition according to claim 7, comprising from 0.5 to 1000 mg of said compound.

9. A pharmaceutical composition according to claim 8, comprising from 2.5 to 250 mg of said compound.

10. A pharmaceutical composition comprising a therapeutically effective amount of the compound according to claim 3, and a pharmaceutical carrier.

11. A pharmaceutical composition according to claim 10, comprising from 0.5 to 1000 mg of said compound.

12. A pharmaceutical composition according to claim 11, comprising from 2.5 to 250 mg of said compound.

* * * * *